United States Patent
Ashida et al.

(10) Patent No.: US 9,102,596 B2
(45) Date of Patent: Aug. 11, 2015

(54) METHOD OF MANUFACTURING 4,4"-DIHYDROXY-M-TERPHENYL

(71) Applicant: Honshu Chemical Industry Co., Ltd., Chuo-ku, Tokyo (JP)

(72) Inventors: Kazuhito Ashida, Wakayama (JP); Yuki Hashimoto, Wakayama (JP); Tomoya Yamamoto, Wakayama (JP); Xuwang Lu, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 14/401,098

(22) PCT Filed: May 14, 2013

(86) PCT No.: PCT/JP2013/063445
§ 371 (c)(1),
(2) Date: Nov. 13, 2014

(87) PCT Pub. No.: WO2013/172352
PCT Pub. Date: Nov. 21, 2013

(65) Prior Publication Data
US 2015/0158800 A1   Jun. 11, 2015

(30) Foreign Application Priority Data
May 14, 2012 (JP) ................................ 2012-110294

(51) Int. Cl.
*C07C 37/06* (2006.01)
*C07C 37/52* (2006.01)
*C07C 37/20* (2006.01)

(52) U.S. Cl.
CPC ................. *C07C 37/06* (2013.01); *C07C 37/20* (2013.01); *C07C 37/52* (2013.01)

(58) Field of Classification Search
CPC ....................................................... C07C 37/06
See application file for complete search history.

(56) References Cited

U.S. PATENT DOCUMENTS

| | | | | |
|---|---|---|---|---|
| 4,877,907 A | * | 10/1989 | Miura et al. | 568/721 |
| 4,939,306 A | * | 7/1990 | Miura et al. | 568/730 |
| 6,872,858 B2 | * | 3/2005 | Muragaki et al. | 568/718 |
| 2006/0030683 A1 | | 2/2006 | Moore et al. | |
| 2012/0092608 A1 | | 4/2012 | Ito et al. | |

FOREIGN PATENT DOCUMENTS

| | | |
|---|---|---|
| JP | 01-168632 A | 7/1989 |
| JP | 2002-234856 A | 8/2002 |
| WO | WO 2010/131600 A1 | 11/2010 |

OTHER PUBLICATIONS

International Search Report issued by Japan Patent Office on Jul. 23, 2013 in the corresponding PCT Application No. PCT/JP2013/063445—11 pages.
Charles C. Price and George P. Mueller, "Condensation of Cyclohexene Oxide, 1,2-Dichlorocyclohexane and 3,4-Dichlorohexane with Anisole," Journal of the American Chemical Society, vol. 66, pp. 628-631, 1944.
Jayaram R. Tagat et al., "Synthetic inhibitors of inteleukin-6 II: 3,5-diaryl pyridines and meta-terphenyls," Bioorganic & Medicinal Chemistry Letters, vol. 5, No. 18, pp. 2143-2146, 1995.

* cited by examiner

*Primary Examiner* — Brian J Davis
(74) *Attorney, Agent, or Firm* — Knobbe, Martens, Olson & Bear LLP

(57) ABSTRACT

In a method of manufacturing 4,4"-dihydroxy-m-terphenyl, a 2-cyclohexene-1-one or 3-hydroxycyclohexane-1-one, and phenol are used as materials, Step (A), Step (B), and Step (C) are implemented in this order, or Step (D) and Step (C) are implemented in this order: Step (A) to obtain a 1,1,3-trisphenol by causing the 2-cyclohexene-1-one or 3-hydroxycyclohexane-1-one and phenol to react with each other in the presence of a catalyst; Step (B) to obtain a bis(4-hydroxyphenyl)cyclohexene by causing the 1,1,3-trisphenol to undergo breakdown reaction; Step (C) to obtain a 4,4"-dihydroxy-m-terphenyl by dehydrogenating the bis(4-hydroxyphenyl)cyclohexene; Step (D) to obtain a bis(4-hydroxyphenyl)cyclohexene by causing the 2-cyclohexene-1-one or 3-hydroxycyclohexane-1-one and phenol to react with each other in the presence of a catalyst.

1 Claim, No Drawings

METHOD OF MANUFACTURING 4,4"-DIHYDROXY-M-TERPHENYL

TECHNICAL FIELD

The present invention relates to a method of manufacturing 4,4"-dihydroxy-m-terphenyl. More specifically, the present invention relates to a method of manufacturing 4,4"-dihydroxy-m-terphenyl that is expected to prove useful in such applications as synthetic resin materials such as polyester, polycarbonate, polyurethane, and the like, photo-resist materials such as display elements, semiconductors, and the like, etc., wherein such method can be easily implemented in industrial settings to obtain a 4,4"-dihydroxy-m-terphenyl by using a 2-cyclohexene-1-one or 3-hydroxycyclohexane-1-one and phenol as materials, and through three steps of Step (A), Step (B) and Step (C) or two steps of Step (D) and Step (C), in this order, respectively.

BACKGROUND ART

Among the conventional manufacturing methods of 4,4"-dihydroxy-m-terphenyl, a method is disclosed, for example, whereby a 4,4"-dihydroxy-m-terphenyl is synthesized by causing a 1,1,3,3-tetrakis(4-hydroxyphenyl)-cyclohexane, which has been synthesized from 1,3-cyclohexane dione and phenol, to undergo breakdown and dehydrogenation reactions (Patent Literature 1). With this method, however, the yield of material tetrakis phenol is extremely low or material tetrakis phenol cannot be synthesized at all.

Also disclosed is a method to synthesize a 4,4"-dihydroxy-m-terphenyl by causing 2-(4-bromophenoxyl)tetrahydro-2H-pyrane and 1,3-dibromobenzene to undergo Grignard reaction, followed by deprotection (Patent Literature 2); and by causing 4-methoxyphenyl boronic acid to react with 1,3-diiodobenzene, followed by deprotection (Patent Literature 3), respectively.

However, these methods are associated with very high manufacturing cost and thus difficult to implement in industrial settings, because special, expensive materials such as organic metal compounds are used and Grignard reaction, etc., must be implemented.

On the other hand, a method to manufacture a dihydroxy-p-terphenyl from a trisphenol is also known (Patent Literature 4), but there is no mention, in this patent literature, of how a trisphenol is manufactured from an unsaturated ketone or how a dihydroxy-m-terphenyl is manufactured.

BACKGROUND ART LITERATURE

Patent Literatures

Patent Literature 1: Japanese Patent Laid-open No. Hei 1-168632
Patent Literature 2: U.S. Patent Laid-open No. 2006/0030683
Patent Literature 3: International Patent Laid-open No. 2010/131600
Patent Literature 4: Japanese Patent Laid-open No. 2002-234856

SUMMARY OF THE INVENTION

Problems to be Solved by the Invention

An object of the present invention is to provide a new method of manufacturing 4,4"-dihydroxy-m-terphenyl, which can be easily implemented in industrial settings.

Means for Solving the Problems

After studying in earnest with the object mentioned above, the inventors of the present invention completed the present invention after finding that the target 4,4"-dihydroxy-m-terphenyl could be obtained by a method that is easily implementable in industrial settings, wherein such method uses a 2-cyclohexene-1-one or 3-hydroxycyclohexane-1-one and phenol as starting materials and comprises, in this order, three reaction steps of causing the starting materials to react with each other (Step A), causing the obtained 1,1,3-tris(hydroxyphenyl)cyclohexane (hereinafter referred to as "1,1,3-trisphenol" depending on the circumstance) to undergo breakdown reaction (Step B) and then causing the obtained bis(4-hydroxyphenyl)cyclohexene to undergo dehydration reaction (Step C), or uses a 2-cyclohexene-1-one or 3-hydroxycyclohexane-1-one and phenol as starting materials and comprises, in this order, two reaction steps of causing the starting materials to react with each other (Step D) and then causing the obtained bis(4-hydroxyphenyl)cyclohexene to undergo dehydration reaction (Step C).

To be specific, the present invention provides a method of manufacturing 4,4"-dihydroxy-m-terphenyl expressed by General Formula (4) below, characterized in that such method uses a 2-cyclohexene-1-one expressed by General Formula (1) below or 3-hydroxycyclohexane-1-one expressed by General Formula (2) below and phenol expressed by General Formula (3) below as materials and implements Step (A), Step (B) and Step (C) below, in this order, or Step (D) and Step (C) below, in this order:

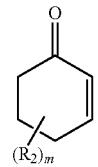

General Formula (1)

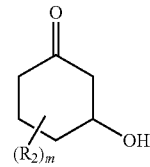

General Formula (2)

(In the formulas, each $R_2$ independently represents an alkyl group, alkoxy group, aromatic hydrocarbon group, or halogen atom, while each m independently indicates 0 or an integer of 1 to 4, where $R_2$ substitution does not occur in the third position when m is 1 or greater, and when m is 2 or greater, $R_2$'s may be identical or different, and $R_2$ substitution does not occur in two positions of the same carbon atom. In addition, $R_2$ and m in General Formula (1) may be identical to or different from $R_2$ and m in General Formula (2), respectively.)

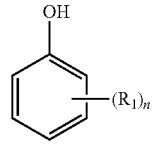

General Formula (3)

(In the formula, each $R_1$ independently represents an alkyl group, alkoxy group, aromatic hydrocarbon group, halogen atom, or hydroxyl group, while n indicates 0 or an integer of 1 to 4, where $R_1$'s may be identical or different when n is 2 or greater.)

Step (A): Step to obtain a 1,1,3-trisphenol expressed by General Formula (5) below by causing the 2-cyclohexene-1-one or 3-hydroxycyclohexane-1-one and phenol to react with each other in the presence of a catalyst.

Step (B): Step to obtain a bis(4-hydroxyphenyl)cyclohexene expressed by General Formula (6) below by causing the 1,1,3-trisphenol to undergo breakdown reaction.

Step (C): Step to obtain a 4,4"-dihydroxy-m-terphenyl by dehydrogenating the bis(4-hydroxyphenyl)cyclohexene.

Step (D): Step to obtain a bis(4-hydroxyphenyl)cyclohexene expressed by General Formula (6) below by causing the 2-cyclohexene-1-one or 3-hydroxycyclohexane-1-one and phenol to react with each other in the presence of a catalyst.

General Formula (4)

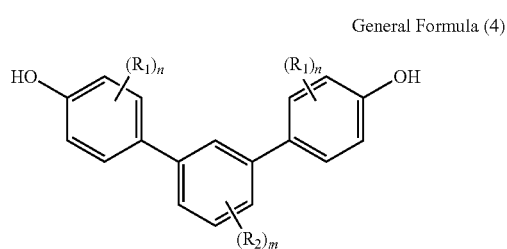

(In the formula, each $R_1$ and n is independently the same as the corresponding items in General Formula (3), respectively, while $R_2$ and m are the same as the corresponding items in General Formula (1) or General Formula (2), respectively.)

General Formula (5)

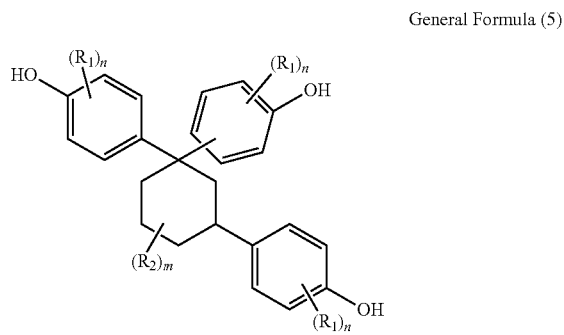

(In the formula, each $R_1$ and n is independently the same as the corresponding items in General Formula (3), respectively, while $R_2$ and m are the same as the corresponding items in General Formula (1) or General Formula (2), respectively.)

General Formula (6)

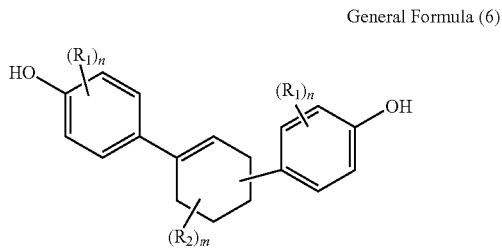

(In the formula, each $R_1$ and n is independently the same as the corresponding items in General Formula (3), respectively, while $R_2$ and m are the same as the corresponding items in General Formula (1) or General Formula (2), respectively, and the binding position of the 4-hydroxyphenyl group having no fixed binding position is the third position or fifth position of the cyclohexene ring.)

Effects of the Invention

The method of manufacturing 4,4"-dihydroxy-m-terphenyl proposed by the present invention uses materials that are readily available in industrial settings and does not require special, expensive materials such as organic metal compounds nor does it require organic halogen compounds that may pollute the environment when disposed of or incinerated. Furthermore, by selecting appropriate materials, reaction conditions, and/or post-reaction processing methods, the target 4,4"-dihydroxy-m-terphenyl can be obtained with high yield under reaction conditions that can be easily achieved in industrial settings.

MODE FOR CARRYING OUT THE INVENTION

The method of manufacturing 4,4"-dihydroxy-m-terphenyl proposed by the present invention is explained in detail below.

According to the method of manufacturing 4,4"-dihydroxy-m-terphenyl proposed by the present invention, a 2-cyclohexene-1-one or 3-hydroxycyclohexane-1-one expressed by one of the formulas below is used as a starting material:

General Formula (1)

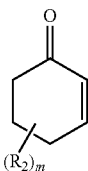

General Formula (2)

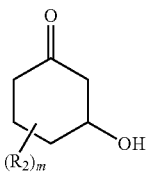

(In the formulas, each $R_2$ independently represents an alkyl group, alkoxy group, aromatic hydrocarbon group, or halogen atom, while each m independently indicates 0 or an integer of 1 to 4, where $R_2$ substitution does not occur in the third position when m is 1 or greater, and when m is 2 or greater, $R_2$'s may be identical or different, and $R_2$ substitution does not occur in two positions of the same carbon atom. In addition, $R_2$ and m in General Formula (1) may be identical to or different from $R_2$ and m in General Formula (2), respectively.)

In the 2-cyclohexene-1-one expressed by General Formula (1) or 3-hydroxycyclohexane-1-one expressed by General Formula (2), $R_2$ independently represents an alkyl group, alkoxy group, aromatic hydrocarbon group, or halogen atom, while m independently indicates 0 or an integer of 1 to 4, where $R_2$ substitution does not occur in the third position when m is 1 or greater, and when m is 2 or greater, $R_2$'s may be identical or different, and $R_2$ substitution does not occur in two positions of the same carbon.

The aforementioned alkyl group is preferably a linear or branched alkyl group having 1 to 12 carbon atoms or cycloalkyl group having 5 to 12 carbon atoms.

A more preferable form of alkyl group is a linear or branched alkyl group having 1 to 8 carbon atoms or a cycloalkyl group having 5 to 6 carbon atoms, while a most preferable form of alkyl group is a linear or branched alkyl group having 1 to 4 carbon atoms. Specific examples of the foregoing include a methyl group, ethyl group, n-propyl group, isopropyl group, n-butyl group, sec-butyl group, t-butyl group, etc. Additionally, the aforementioned cycloalkyl group having 5 to 12 carbon atoms may be a cyclohexyl group, cyclopentyl group, or cycloheptyl group, for example.

Also, the aforementioned alkyl group may be substituted by a halogen atom, alkoxy group, phenyl group, oxygen atom (cyclic ether group), etc., to the extent that the substitution does not interfere with the effects of the present invention, or it may not be substituted. Specific examples include a benzyl group, methoxy ethyl group, 3-chloropropyl group, etc.

The aforementioned alkoxy group is preferably a linear or branched alkoxy group having 1 to 12 carbon atoms or a cycloalkoxy group having 5 to 12 carbon atoms.

A more preferable form of alkoxy group is a linear or branched alkoxy group having 1 to 8 carbon atoms or cycloalkoxy group having 5 to 6 carbon atoms, while a most preferable form of alkoxy group is a linear or branched alkoxy group having 1 to 4 carbon atoms. Specific examples of the foregoing include a methoxy group, ethoxy group, n-propoxy group, n-butoxy group, t-butoxy group, etc. Additionally, the aforementioned cycloalkoxy group having 5 to 12 carbon atoms may be a cyclopentyloxy group or a cyclohexyloxy group, for example. Also, the aforementioned alkoxy group may be substituted by a halogen atom, alkoxy group, phenyl group, etc., to the extent that the substitution does not interfere with the effects of the present invention, or it may not be substituted. Specific examples include a 2-phenyl ethoxy group, methoxy ethoxy group, 2-chloroethoxy group, etc.

In addition, the aforementioned aromatic hydrocarbon group is preferably an aromatic hydrocarbon group having 6 to 12 carbon atoms. For example, it may be a phenyl group, phenyloxy group, 1-naphtyl group, or the like.

Also, the aforementioned aromatic hydrocarbon group may be substituted by an alkyl group, alkoxy group, phenyl group, halogen atom, etc., to the extent that the substitution does not interfere with the effects of the present invention, or it may not be substituted. Specific examples include a 4-methyl phenyl group, 4-chlorophenyl group, etc.

The aforementioned halogen atom may be a fluorine atom, chlorine atom, bromine atom, iodine atom, etc., for example.

In addition, each m independently indicates 0 or an integer of 1 to 4, or preferably 0 or 1 to 3, or more preferably 0 or 1 to 2, or most preferably 0. When m is 2 or greater, $R_2$'s may be identical or different.

In addition, in the 2-cyclohexene-1-one expressed by General Formula (1) above, the substitution group expressed by $R_2$ preferably substitutes in the fourth position or/and fifth position, and preferably the substitution group is not present in the second position.

Accordingly, specific examples of the aforementioned 2-cyclohexene-1-one include 2-cyclohexene-1-one, 6-methyl-2-cyclohexene-1-one, 6-fluoro-2-cyclohexene-1-one, 2-methyl-2-cyclohexene-1-one, 2-methoxy-2-cyclohexene-1-one, 2-chloro-2-cyclohexene-1-one, 4-methyl-2-cyclohexene-1-one, 4-ethyl-2-cyclohexene-1-one, 4-isopropyl-2-cyclohexene-1-one, 4-t-butyl-2-cyclohexene-1-one, 4-cyclohexyl-2-cyclohexene-1-one, 4-phenyl-2-cyclohexene-1-one, 4-phenyl methyl-2-cyclohexene-1-one, 5-methyl-2-cyclohexene-1-one, 5-ethyl-2-cyclohexene-1-one, 5-isopropyl-2-cyclohexene-1-one, 5-t-butyl-2-cyclohexene-1-one, 5-n-butyl-2-cyclohexene-1-one, 5-phenyl-2-cyclohexene-1-one, 2,6-dimethyl-2-cyclohexene-1-one, 4,5-dimethyl-2-cyclohexene-1-one, 5-isopropyl-2-methyl-2-cyclohexene-1-one, 2-isopropyl-5-methyl-2-cyclohexene-1-one, 2,5,6-trimethyl-2-cyclohexene-1-one, etc.

Such 2-cyclohexene-1-one can be easily obtained by a known method, such as a method to isomerize a 2-alkylidenecycloalkanone in the presence of an acid catalyst and platinum catalyst (Japanese Patent Laid-open No. Sho 58-42175, etc.), a method to dehydrate and isomerize a 2-(1-hydroxylalkyl)cycloalkanone in the presence of an acid catalyst, etc. (Japanese Patent Laid-open No. Sho 56-147740, etc.) or a method to cyclize and condense a dicarbonyl compound (Japanese Patent Laid-open No. Hei 10-130192, etc.), for example.

In addition, in the 3-hydroxycyclohexane-1-one expressed by General Formula (2) above, the substitution group expressed by $R_2$ preferably substitutes in the fourth position or/and fifth position, and preferably the substitution group is not present in the second position.

Accordingly, specific examples of the aforementioned 3-hydroxycyclohexane-1-one include 3-hydroxycyclohexane-1-one, 6-methyl-3-hydroxycyclohexane-1-one, 6-fluoro-3-hydroxycyclohexane-1-one, 2-methyl-3-hydroxycyclohexane-1-one, 2-ethyl-3-hydroxycyclohexane-1-one, 2-methoxy-3-hydroxycyclohexane-1-one, 2-chloro-3-hydroxycyclohexane-1-one, 4-methyl-3-hydroxycyclohexane-1-one, 4-ethyl-3-hydroxycyclohexane-1-one, 4-isopropyl-3-hydroxycyclohexane-1-one, 4-t-butyl-3-hydroxycyclohexane-1-one, 4-cyclohexyl-3-hydroxycyclohexane-1-one, 4-phenyl-3-hydroxycyclohexane-1-one, 4-phenyl methyl-3-hydroxycyclohexane-1-one, 5-methyl-3-hydroxycyclohexane-1-one, 5-ethyl-3-hydroxycyclohexane-1-one, 5-isopropyl-3-hydroxycyclohexane-1-one, 5-t-butyl-3-hydroxycyclohexane-1-one, 5-n-butyl-3-hydroxycyclohexane-1-one, 5-phenyl-3-hydroxycyclohexane-1-one, 2,6-dimethyl-3-hydroxycyclohexane-1-one, 4,5-dimethyl-3-hydroxycyclohexane-1-one, 5-isopropyl-2-methyl-3-hydroxycyclohexane-1-one, 2-isopropyl-5-methyl-3-hydroxycyclohexane-1-one, 2,5,6-trimethyl-3-hydroxycyclohexane-1-one, etc.

Such 3-hydroxycyclohexane-1-one can be easily obtained by a known method, such as a method to cyclize and hydrogenate a multivalent hydroxy alkyl phenol in the presence of a hydrogenating catalyst, etc. (Japanese Patent Laid-open No. Hei 11-60534, etc.).

Under the method of manufacturing 4,4"-dihydroxy-m-terphenyl proposed by the present invention, a phenol expressed by General Formula (3) is also used as a starting material.

General Formula (3)

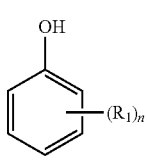

(In the formula, each $R_1$ independently represents an alkyl group, alkoxy group, aromatic hydrocarbon group, halogen atom, or hydroxyl group, while n indicates 0 or an integer of 1 to 4, where $R_1$'s may be identical or different when n is 2 or greater.)

In the phenol expressed by General Formula (3) above, each $R_1$ independently represents an alkyl group, alkoxy group, aromatic hydrocarbon group, halogen atom, or hydroxyl group, while n indicates 0 or an integer of 1 to 4, where $R_1$'s may be identical or different when n is 2 or greater.

Specific examples, preferable ranges and preferable examples of the aforementioned alkyl group, alkoxy group, aromatic hydrocarbon group, and halogen atom are the same as the specific examples, preferable ranges and preferable examples of the alkyl group, alkoxy group, aromatic hydrocarbon group, and halogen atom represented by $R_2$ in General Formula (1) or General Formula (2). In addition, the substitution groups that may substitute the alkyl group, alkoxy group, and aromatic hydrocarbon group represented by $R_1$, and specific examples thereof, are also the same as the substitution groups and specific examples thereof as explained in connection with $R_2$ to the extent that they do not lessen the effects of the present invention, or there may not be any substitution group. In addition, n is preferably 0 or 1 to 3, or more preferably 0 or 1 to 2, or most preferably 0. When n is 2 or greater, $R_1$'s may be identical or different.

In addition, the substitution group represented by $R_1$ does not substitute the para-position of the hydroxyl group. The substitution position is preferably the ortho-position of the hydroxyl group, or more preferably the substitution group $R_1$ is absent in at least one or both of the metha-positions of the hydroxyl group, or most preferably there is no substitution group in either position.

In addition, preferably the substitution group in the metha-position of the hydroxyl group is a methyl group or methoxy group.

Accordingly, a preferable phenol is expressed by General Formula (7) below:

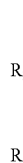

General Formula (7)

(In the formula, $R_3$ and $R_5$ each represent a hydrogen atom, alkyl group, alkoxy group, aromatic hydrocarbon group, or halogen atom, while $R_4$ represents a hydrogen atom, alkyl group, alkoxy group, aromatic hydrocarbon group, halogen atom, or hydroxyl group.)

In General Formula (7) above, $R_3$ and $R_5$ each represent a hydrogen atom, alkyl group, alkoxy group, aromatic hydrocarbon group, or halogen atom, while $R_4$ represents a hydrogen atom, alkyl group, alkoxy group, aromatic hydrocarbon group, halogen atom, or hydroxyl group, where specific examples, preferable ranges, and preferable examples of $R_3$, $R_4$, and $R_5$ when they are an alkyl group, alkoxy group, aromatic hydrocarbon group, or halogen atom are the same as the specific examples, preferable ranges and preferable examples of the alkyl group, alkoxy group, aromatic hydrocarbon group, or halogen atom as explained in connection with $R_2$. In addition, the substitution groups that may substitute the alkyl group, alkoxy group, and aromatic hydrocarbon group represented by $R_3$, $R_4$, or $R_5$, and specific examples thereof, are also the same as the substitution groups and specific examples thereof as explained in connection with $R_2$ to the extent that they do not lessen the effects of the present invention, or there may not be any substitution.

In addition, preferably neither $R_3$ nor $R_4$ is a tertiary alkyl group, and when one is a tertiary alkyl group, more preferably the other is a hydrogen atom, primary alkyl group, or secondary alkyl group.

Also when an aromatic hydrocarbon group is used for $R_3$ and $R_4$, preferably only one of $R_3$ and $R_4$ is an aromatic hydrocarbon group.

Also from the viewpoint of yield, preferably $R_5$ is a hydrogen atom when it is used as the material in Step (A), and preferably $R_5$ is not a hydrogen atom, or specifically it is an alkyl group, alkoxy group, aromatic hydrocarbon group, or halogen atom, or more preferably an alkyl group or alkoxy group, or most preferably a methyl group or methoxy group, when it is used as the material in Step (D).

Accordingly, specific examples of the phenol include phenol, catechol, o-cresol, m-cresol, 2-ethhylphenol, 2,5-xylenol, 2,6-xylenol, 2,3,6-trimethyl phenol, 2-cyclohexyl phenol, 2-cyclopentylphenol, 2-phenylphenol, 2-n-propylphenol, 2-isopropylphenol, 3-isopropylphenol, 2,6-diisopropylphenol, 2-t-butylphenol, 2-t-butyl-6-methylphenol, 2-sec-butylphenol, 2-isobutylphenol, 2-chlorophenol, 2-methoxyphenol, 5-methyl-2-t-butylphenol, 5-methyl-2-cyclohexylphenol, etc.

Under the method of manufacturing 4,4"-dihydroxy-m-terphenyl proposed by the present invention, the target 4,4"-dihydroxy-m-terphenyl can be obtained by a method that uses a 2-cyclohexene-1-one expressed by General Formula (1) above or 3-hydroxycyclohexane-1-one expressed by General Formula (2) above and phenol expressed by General Formula (3) above as starting materials and comprises, in this order, Step (A) to cause the 2-cyclohexene-1-one or 3-hydroxycyclohexane-1-one and phenol to react with each other in the presence of a catalyst and thereby obtain a 1,1,3-trisphenol expressed by General Formula (5) below, Step (B) to cause the 1,1,3-trisphenol to undergo breakdown reaction and thereby obtain a bis(4-hydroxyphenyl)cyclohexene expressed by General Formula (6) above, and Step (C) to dehydrogenate the bis(4-hydroxyphenyl)cyclohexene and thereby obtain a 4,4"-dihydroxy-m-terphenyl, or, in this order, Step (D) to cause the 2-cyclohexene-1-one or 3-hydroxycyclohexane-1-one and phenol to react with each other in the presence of a catalyst and thereby obtain a bis(4-hydroxyphenyl)cyclohexene expressed by General Formula (6) above, and Step (C) above.

Under the manufacturing method proposed by the present invention, Step (A) is to cause the 2-cyclohexene-1-one or 3-hydroxycyclohexane-1-one and phenol to react with each other in the presence of a catalyst and thereby obtain a 1,1,3-trisphenol expressed by General Formula (5) below:

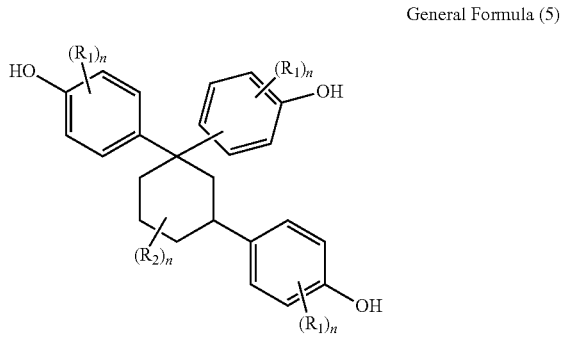

General Formula (5)

(In the formula, each $R_1$ and n is independently the same as the corresponding items in General Formula (3), respectively, while $R_2$ and m are the same as the corresponding items in General Formula (1) or General Formula (2), respectively, and the substitution position of the hydroxyphenyl group having no fixed substitution position is the para-position or ortho-position of the hydroxyl group.)

In General Formula (5) above, $R_1$ and n are the same as the corresponding items in General Formula (3), respectively, while $R_2$ and m are the same as the corresponding items in General Formula (1) or General Formula (2), respectively. In addition, $R_2$ does not substitute the carbon atom of the hydroxy-phenyl-group-substituted cyclohexane ring, and when m is 2 or greater, $R_2$'s do not substitute the same carbon atom. A preferable substitution position of $R_2$ is the fourth position and/or fifth position of the cyclohexane-1,1,3-triyl group (1,1,3-cyclohexane ring).

Also in the formula, the binding position of the hydroxyphenyl group having no fixed binding position (one of the two hydroxyphenyl groups binding with the carbon atom in the first position of the cyclohexane ring) to the cyclohexane ring is the ortho-position or para-position with respect to the phenyl-group-substituted hydroxyl group.

If the binding position is the ortho-position, preferably at least one ortho-position of the hydroxyl group is not substituted for the other hydroxyphenyl group.

In addition, with respect to the 1,1,3-trisphenol, preferably all hydroxyphenyl groups have carbon atoms in the para-positions with respect to the hydroxyl groups binding to the cyclohexane ring, and preferably the substitution position of $R_1$ is the ortho-position with respect to the hydroxyl group.

A preferable form of 1,1,3-trisphenol is expressed by General Formula (8) or General Formula (9) below:

General Formula (8)

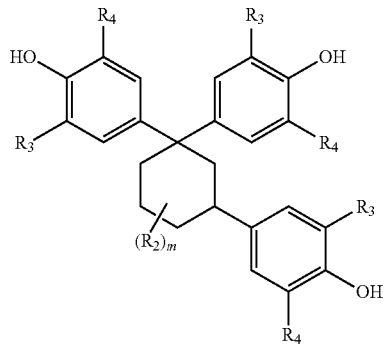

General Formula (9)

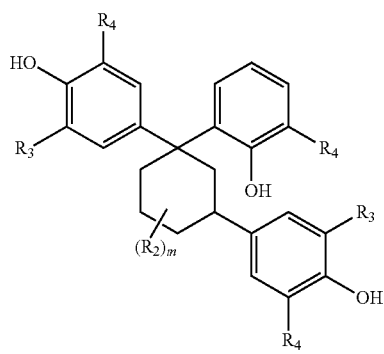

(In the formula, $R_2$ and m are the same as the corresponding items in General Formula (1) or General Formula (2), respectively, while each $R_3$ and $R_4$ are independently the same as the corresponding items in General Formula (7), respectively.)

Accordingly, specific examples of the 1,1,3-trisphenol include 1,1,3-tris(4-hydroxyphenyl)cyclohexane, 1,1,3-tris(3-methyl-4-hydroxyphenyl)cyclohexane, 1,1,3-tris(3-ethyl-4-hydroxyphenyl)cyclohexane, 1,1,3-tris(3-isopropyl-4-hydroxyphenyl)cyclohexane, 1,1,3-tris(3-n-propyl-4-hydroxyphenyl)cyclohexane, 1,1,3-tris(3-tert-butyl-4-hydroxyphenyl)cyclohexane, 1,1,3-tris(3-sec-butyl-4-hydroxyphenyl)cyclohexane, 1,1,3-tris(3-chloro-4-hydroxyphenyl)cyclohexane, 1,1,3-tris(3,5-dimethyl-4-hydroxyphenyl)cyclohexane, 1,1,3-tris(3-tert-butyl-5-methyl-4-hydroxyphenyl)cyclohexane, 1,1,3-tris(3,5-diisopropyl-4-hydroxyphenyl)cyclohexane, 1,1,3-tris(3-phenyl-4-hydroxyphenyl)cyclohexane, 1,1,3-tris(3,4-dihydroxyphenyl)cyclohexane, 1,1,3-tris(3-cyclohexyl-4-hydroxyphenyl)cyclohexane, 1,1,3-tris(3-isopropyl-5-methyl-4-hydroxyphenyl)cyclohexane, 1,1,3-tris(4-hydroxyphenyl)-6-methylcyclohexane, 1,1,3-tris(4-hydroxyphenyl)-2-methylcyclohexane, 1,1,3-tris(4-hydroxyphenyl)-2-methoxycyclohexane, 1,1,3-tris(4-hydroxyphenyl)-4-methylcyclohexane, 1,1,3-tris(4-hydroxyphenyl)-4-phenylcyclohexane, 1,1,3-tris(4-hydroxyphenyl)-4-cyclohexylcyclohexane, 1,1,3-tris(4-hydroxyphenyl)-5-methylcyclohexane, 1,1,3-tris(4-hydroxyphenyl)-5-t-butylcyclohexane, 1,1,3-tris(4-hydroxyphenyl)-5-phenylcyclohexane, 1,1,3-tris(4-hydroxyphenyl)-2-methyl-5-isopropyl cyclohexane, 1,1,3-tris(4-hydrdoxyphenyl)-2,5,6-trimethylcyclohexane, 1,3-bis(4-hydroxyphenyl)-1-(2-hydroxyphenyl)cyclohexane, 1,3-bis(3-methyl-4-hydroxyphenyl)-1-(3-methyl-2-hydroxyphenyl)cyclohexane, etc.

In Step (A), a 1,1,3-trisphenol can be obtained in one reaction step by causing a 2-cyclohexene-1-one or 3-hydroxycyclohexane-1-one and phenol to react with each other in the presence of a catalyst.

For example, the reaction to obtain a 1,1,3-trisphenol by causing a phenol and 2-cyclohexene-1-one or 3-hydroxycyclohexane-1-one to react with each other is indicated by Reaction Formula (1) below:

Reaction Formula (1)

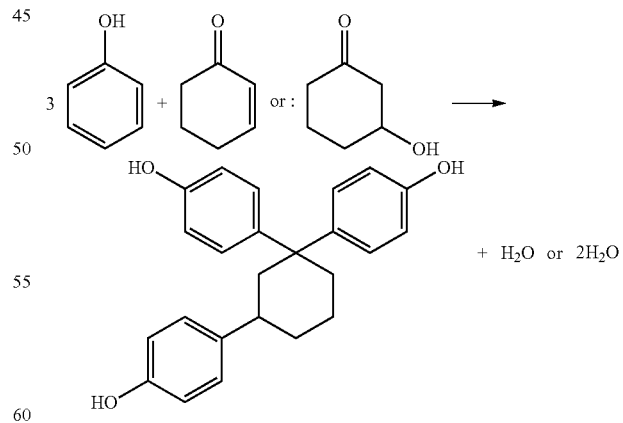

If two or more types of phenols according to General Formula (3) are caused to react either simultaneously or successively, then mixed trisphenols whose three hydroxyphenyl groups have different or identical substitution groups, substitution positions, and/or substitution numbers will be produced.

When a phenol expressed by General Formula (3) and 2-cyclohexene-1-one expressed by General Formula (1) or 3-hydroxycyclohexane-1-one expressed by General Formula (2) are caused to react with each other under the manufacturing method proposed by the present invention, the phenol is used preferably by a range of 3 to 50 times by mol, or more preferably by a range of 5 to 30 times by mol, or most preferably by a range of 8 to 20 times by mol, relative to the 2-cyclohexene-1-one or 3-hydroxycyclohexane-1-one, but the quantity of phenol is not limited to the foregoing.

Under the manufacturing method proposed by the present invention, preferably the aforementioned catalyst is an acid catalyst. However, the catalyst is not limited to the foregoing.

The acid catalyst may be a gaseous, liquid, or solid acid catalyst such as a proton acid catalyst, Lewis acid catalyst, or the like, for example.

Specific examples include inorganic acids such as hydrogen chloride gas, hydrochloric acid, sulfuric acid, phosphoric acid, sulfuric anhydride, and the like; organic acids such as p-toluene sulfonic acid, methane sulfonic acid, trifluoromethane sulfonic acid, trichloroacetic acid, and the like; halogenated metals such as aluminum chloride, iron chloride, and the like; heteropoly acids such as phosphotungstic acid, silicotungstic acid, and the like; solid acids such as cation exchange resins, etc.

Among the aforementioned catalysts, hydrochloric acid and hydrogen chloride gas are most preferable.

The use quantity of acid catalyst is not limited in any way. There is no single definition of preferable use quantity because an appropriate quantity varies from one catalyst to another, but in the case of 35% hydrochloric acid, for example, the acid catalyst is used by a range of preferably 0.1 to 3 times by mol, or more preferably 0.2 to 1.0 time by mol, or most preferably 0.3 to 0.6 time by mol, relative to the 2-cyclohexene-1-one or 3-hydroxycyclohexane-1-one.

Furthermore, under the manufacturing method proposed by the present invention, an auxiliary catalyst may be used to accelerate the reaction. The reaction will progress without an auxiliary catalyst, but it is preferable to use an auxiliary catalyst from the viewpoint of reaction yield and reaction speed.

Preferably the auxiliary catalyst is a compound or high-polymer compound having a mercapto group, or specifically alkyl mercaptan such as methyl mercaptan, ethyl mercaptan, n-octyl mercaptan, n-dodecyl mercaptan, or the like, or mercaptan carboxylic acid such as mercaptoacetic acid, β-mercaptopropyonic acid or the like, or cation exchange resin or organic high-polymer siloxane having a mercapto group, or the like, for example.

If methyl mercaptan is used, it may be used in the form of aqueous solution of sodium salt. The use quantity of auxiliary catalyst is not limited in any way, and there is no single definition because an appropriate quantity varies depending on the reaction conditions and type, but if alkyl mercaptan is used, for example, its use quantity is in a range of preferably 0.5 to 50 percent by mol, or more preferably 2 to 30 percent by mol, or most preferably 4 to 20 percent by mol, relative to the 2-cyclohexene-1-one or 3-hydroxycyclohexane-1-one.

The reaction temperature is in a range of preferably 0 to 80° C., or more preferably 10 to 60° C., or most preferably 15 to 50° C.

Under these reaction conditions, preferably the reaction is completed within 80 hours or so after adding all materials to the reaction system.

A reaction solvent may or may not be used for the reaction, but if the phenol has a high melting point or otherwise the materials and catalyst do not mix fully, it is preferable to use a reaction solvent.

If the material phenol is in liquid state at the time of reaction, for example, the phenol itself will serve as a solvent and other solvent may not necessarily be required.

When a reaction solvent is used, the type and additive quantity of solvent are not limited in any way so long as the effects of the present invention are not inhibited, but specific examples of preferable reaction solvents include water, methanol, ethanol, 1-propanol, 2-propanol, and other lower aliphatic alcohols; toluene, xylene, and other aromatic hydrocarbons; tetrahydrofuran, dioxysolane, and other ethers; hexane, heptane, cyclohexane, and other saturated aliphatic hydrocarbons; and mixed solvent of the foregoing.

Preferably the reaction solvent is used by a range of 0.1 to 20 times by mol relative to the 2-cyclohexene-1-one or 3-hydroxycyclohexane-1-one.

How the reaction materials are added for the reaction is not limited in any way. For example, the materials, catalyst, and auxiliary catalyst and/or reaction solvent if necessary, may be introduced to the reaction container all at once, after which the mixture may be heated to the reaction temperature in an ambience of inert gas to cause reaction under agitation. Alternatively, the material ketone, or 2-cyclohexene-1-one or 3-hydroxycyclohexane-1-one to be specific, or mixed liquid of this material ketone and phenol or solvent, may be added successively, at the reaction temperature, to the reaction container in which the material phenol, acid catalyst, and auxiliary catalyst and/or reaction solvent if necessary have been introduced. The latter method is preferable from the viewpoint of reaction yield.

According to a preferable embodiment, the specified quantities of phenol, acid catalyst, and auxiliary catalyst and/or reaction solvent if necessary, are introduced to the reaction container and the mixture is heated to the specified reaction temperature under nitrogen streams and agitation, after which the 2-cyclohexene-1-one or 3-hydroxycyclohexane-1-one is successively added, for example.

Assume that a 3-hydroxycyclohexane-1-one is used as the material ketone for the reaction under the manufacturing method proposed by the present invention; although the details of the reaction are unclear, the 3-hydroxycyclohexane-1-one produces a 2-cyclohexene-1-one in the presence of acid, for example, and therefore a 1,1,3-tris(hydroxyphenyl)cycloalkane may be produced during the reaction by way of a 2-cycloalkene-1-one.

It is also possible, after the end of reaction, to not separate the reaction product 1,1,3-trisphenol from the obtained resultant liquid of reaction, but to use the reaction mixture directly as the material for the next step, or Step (B), where the 1,1,3-trisphenol is caused to undergo breakdown reaction to obtain a bis(4-hydroxyphenyl)cyclohexene expressed by General Formula (6) below.

Notwithstanding the above, preferably the 1,1,3-trisphenol is collected at an appropriate level of purity. In this case, after the end of reaction, by applying any known isolation or purification method as deemed appropriate, post treatment such as neutralization and water washing may be conducted.

For example, aqueous alkali solution such as aqueous sodium hydroxide solution, aqueous ammonia solution, or the like is added to the resultant liquid of reaction to neutralize the acid catalyst.

Thereafter, solvent that separates from water is added, such as aromatic hydrocarbon, aliphatic ketone, or the like, if necessary, to separate and remove the water layer, after which the obtained oil layer is cooled and crystallized or precipitated and then filtered out to obtain a 1,1,3-trisphenol in crude crystal or solid state.

It is also possible, if necessary, to add water again to the aforementioned oil layer obtained from separating and removing the water layer, and agitate and water-wash the mixture and then separate and remove the water layer, and after performing this operation once or repeating it multiple times, cool the obtained oil layer to be crystallized or precipitated and then filtered out to obtain a trisphenol in crude crystal or solid state. It is also possible to distill the aforementioned oil layer obtained from separating and removing the water layer to distill out the solvent and unreacted phenol, and then dissolve the residual liquid in an appropriate solvent and cool the obtained solution to be crystallized or precipitated and then filtered, or if crystallizing the trisphenol is difficult, by cooling the distillation residue, the trisphenol can be obtained in crude state. In the above crystallization step, the 1,1,3-trisphenol, depending on its type, may be obtained as an adduct crystal with the solvent or material phenol used. In addition, the obtained crystal, solid, or crude product may be purified further using any known purification method such as crystallization and used in such purer form as the material for the next step.

For the material for the next step, or Step (B), preferably a 1,1,3-trisphenol obtained through crystallization or precipitation followed by filtering, as mentioned above, is used.

Under the manufacturing method proposed by the present invention, Step (B) that follows Step (A) mentioned above is where the 1,1,3-trisphenol obtained in Step (A) is caused to undergo breakdown reaction to obtain a bis(4-hydroxyphenyl)cyclohexene expressed by General Formula (6) below. On the other hand, Step (D) is where a 2-cyclohexene-1-one or 3-hydroxycyclohexane-1-one and phenol are caused to react with each other in the presence of a catalyst to obtain a bis(4-hydroxyphenyl)cyclohexene expressed by General Formula (6) below through a single reaction:

General Formula (6)

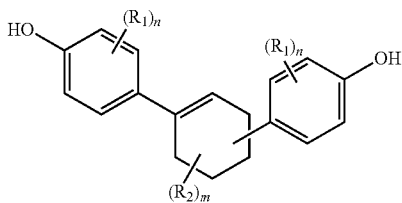

(In the formula, each $R_1$ and n is independently the same as the corresponding items in General Formula (3), respectively, while $R_2$ and m are the same as the corresponding items in General Formula (1) or General Formula (2), respectively, and the binding position of the 4-hydroxyphenyl group having no fixed binding position is the third position or fifth position of the cyclohexene ring.)

Accordingly, the bis(4-hydroxyphenyl)cyclohexene is specifically a 1,3-bis(4-hydroxyphenyl)cyclohexene expressed by General Formula (10) below or 1,5-bis(4-hydroxyphenyl)cyclohexene expressed by General Formula (11) below:

General Formula (10)

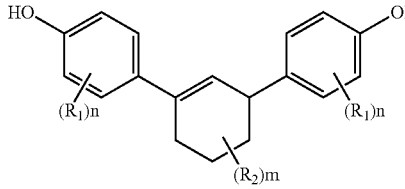

(In the formula, each $R_1$ and n is independently the same as the corresponding items in General Formula (3), respectively, while $R_2$ and m are the same as the corresponding items in General Formula (1) or General Formula (2), respectively.)

General Formula (11)

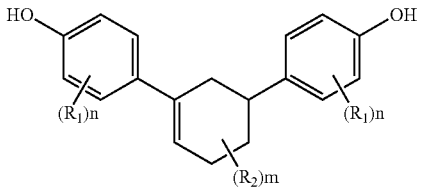

(In the formula, each $R_1$ and n is independently the same as the corresponding items in General Formula (3), respectively, while $R_2$ and m are the same as the corresponding items in General Formula (1) or General Formula (2), respectively.)

In addition, a preferable substitution position of $R_1$ is the same as that in General Formula (3), while a preferable substitution position of $R_2$ is the fourth position or fifth position of the 1-cyclohexene-1,3-diyl group at the center or third position or fourth position of the 1-cyclohexene-1,5-diyl group at the center, and when m is 2 or greater, two $R_2$ substitutions do not occur on the same carbon atom of the cyclohexene-diyl group.

A preferable 1,3- or 1,5-bis(4-hydroxyphenyl)cyclohexene is expressed by General Formula (12) or General Formula (13) below:

General Formula (12)

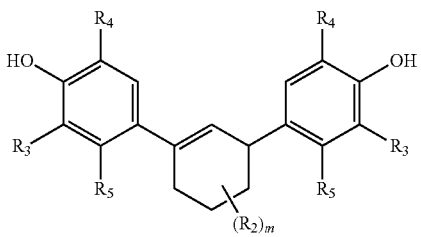

(In the formula, $R_2$ and m are the same as the corresponding items in General Formula (1) or General Formula (2), respectively, while each $R_3$, $R_4$, and $R_5$ are independently the same as the corresponding items in General Formula (7).)

General Formula (13)

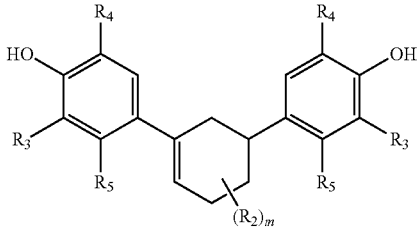

(In the formula, $R_2$ and m are the same as the corresponding items in General Formula (1) or General Formula (2), respectively, while each $R_3$, $R_4$, and $R_5$ are independently the same as the corresponding items in General Formula (7).)

Accordingly, examples include 1,3-bis(4-hydroxyphenyl)-1-cyclohexene, 1,5-bis(4-hydroxyphenyl)-1-cyclohexene, 1,3-bis(3-methyl-4-hydroxyphenyl)-1-cyclohexene, 1,5-bis (3-methyl-4-hydroxyphenyl)-1-cyclohexene, 1,3-bis(3-t-butyl-4-hydroxyphenyl)-1-cyclohexene, 1,5-bis(3-t-butyl-4-hydroxyphenyl)-1-cyclohexene, 1,3-bis(2,5-dimethyl-4-hydroxyphenyl)-1-cyclohexene, 1,5-bis(2,5-dimethyl-4-hydroxyphenyl)-1-cyclohexene, 1,3-bis(2-methyl-5-t-butyl-4-hydroxyphenyl)-1-cyclohexene, 1,5-bis(2-methyl-5-t-butyl-4-hydroxyphenyl)-1-cyclohexene, 1,3-bis(2-methyl-5-cyclohexyl-4-hydroxyphenyl)-1-cyclohexene, 1,5-bis(2-methyl-5-cyclohexyl-4-hydroxyphenyl)-1-cyclohexene, 1,3-bis(2,3,5-trimethyl-4-hydroxyphenyl)-1-cyclohexene, 1,5-bis(2,3,5-trimethyl-4-hydroxyphenyl)-1-cyclohexene, 1,3-bis(3,5-dimethyl-4-hydroxyphenyl)-1-cyclohexene, 1,5-bis (3,5-dimethyl-4-hydroxyphenyl)-1-cyclohexene, 1,3-bis(3-cyclohexyl-4-hydroxyphenyl)-1-cyclohexene, 1,5-bis(3-cyclohexyl-4-hydroxyphenyl)-1-cyclohexene, 1,3-bis(3-phenyl-4-hydroxyphenyl)-1-cyclohexene, 1,5-bis(3-phenyl-4-hydroxyphenyl)-1-cyclohexene, 1,3-bis(3,4-dihydroxyphenyl)-1-cyclohexene, 1,5-bis(3,4-dihydroxyphenyl)-1-cyclohexene, 1,3-bis(4-hydroxyphenyl)-5-methyl-1-cyclohexene, 1,5-bis(4-hydroxyphenyl)-3-methyl-1-cyclohexene, 1,3-bis(4-hydroxyphenyl)-4-methyl-1-cyclohexene, 1,5-bis(4-hydroxyphenyl)-4-methyl-1-cyclohexene, 1,3-bis(4-hydroxyphenyl)-2-methyl-1-cyclohexene, 1,5-bis(4-hydroxyphenyl)-6-methyl-1-cyclohexene, etc.

In Step (B), a 1,1,3-trisphenol is caused to undergo breakdown reaction to produce a bis(4-hydroxyphenyl)cyclohexene.

An example is shown below using Reaction Formula (2). The bis(4-hydroxyphenyl)cyclohexene expressed by General Formula (6) above as produced from this reaction is normally obtained in the form of an isomeric mixture of a 1,3-bis(4-hydroxyphenyl)cyclohexene expressed by General Formula (10) above or 1,5-bis(4-hydroxyphenyl)cyclohexene expressed by General Formula (11) above.

or the like; carbonate of alkali metal such as sodium carbonate, potassium carbonate, or the like; hydrogen carbonate of alkali metal such as sodium hydrogen carbonate, potassium hydrogen carbonate, or the like; phenoxide of alkali metal such as sodium phenoxide, potassium phenoxide, or the like; or hydroxide of alkali earth metal such as magnesium hydroxide, calcium hydroxide, barium hydroxide, or the like. Among these, sodium hydroxide or potassium hydroxide is favorably used.

If such alkali catalyst is used, the alkali catalyst is used by a range of preferably 0.01 to 50 mol, or more preferably 0.1 to 20 mol, per 100 mol of the 1,1,3-trisphenol. The form in which the alkali catalyst is used is not limited in any way, but preferably it is used as an aqueous solution of 10 to 50 percent by weight in the sense that, this way, the alkali catalyst can be introduced with ease.

If the aforementioned starting material 1,1,3-trisphenol or reaction product bis(4-hydroxyphenyl)cyclohexene has a high melting point, or the viscosity of the reaction liquid is high, or otherwise the homogeneity of the materials and catalyst is lost in the reaction container at the breakdown reaction temperature, then preferably the aforementioned breakdown reaction of 1,1,3-trisphenol is implemented in the presence of a reaction solvent in order to improve this situation and further to prevent the produced target substance from undergoing thermal polymerization.

Any reaction solvent can be used without limitation so long as it is inert at the breakdown reaction temperature and not distilled out of the reaction mixture; however, polyethylene glycol such as triethylene glycol, tetraethylene glycol, pentaethylene glycol, or the like, polypropylene glycol such as tripropylene glycol, tetrapropylene glycol, or the like, polyalcohol such as glycerin or the like, or commercially available organic heating medium such as Therm-S(Nippon Steel Chemical Co., Ltd.) or SK-OIL (Soken Chemical & Engineering Co., Ltd.), may be used, for example.

Reaction Formula (2)

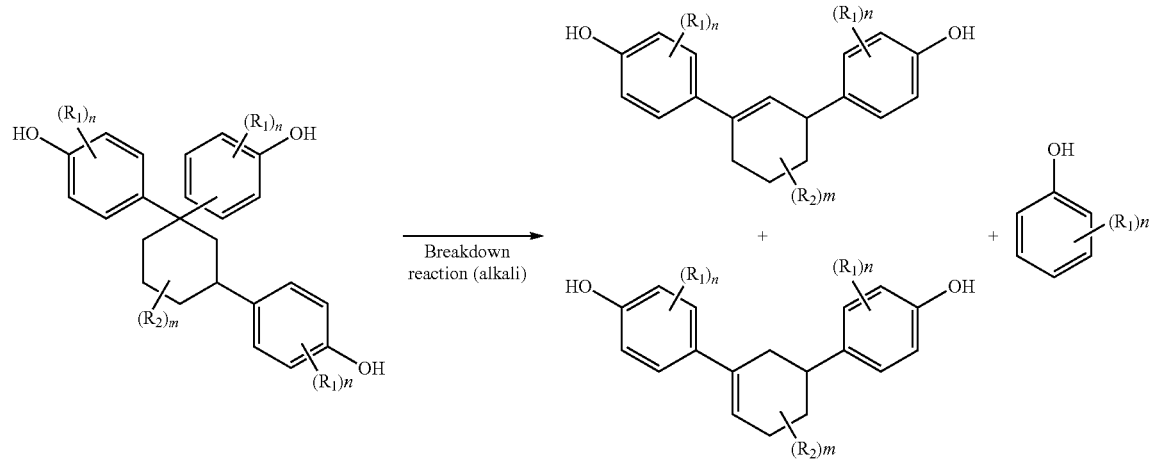

The breakdown reaction of the 1,1,3-trisphenol expressed by General Formula (5) above may be implemented in the absence of catalyst, but preferably it is implemented in the presence of an acid catalyst or basic catalyst. More preferably it is implemented in the presence of a basic catalyst. The basic catalyst is not limited in any way, but it may be, for example, an alkali catalyst such as hydroxide of alkali metal such as sodium hydroxide, potassium hydroxide, lithium hydroxide Such solvent is used by a range of preferably 5 to 150 parts by weight, or more preferably 20 to 100 parts by weight, per 100 parts by weight of the 1,1,3-trisphenol used.

The breakdown reaction of 1,1,3-trisphenol is implemented at a temperature preferably in a range of 150 to 250° C., or more preferably in a range of 160 to 200° C. This is because the reaction speed becomes too slow when the breakdown reaction temperature is too low, while many undesirable side reactions occur when the breakdown reaction temperature is too high. In addition, the breakdown reaction pressure, although not limited in any way, is preferably in a range of normal pressure to reduced pressure, such as 0.13 to 101.32 kPa, or more preferably in a range of 1 to 10 kPa, because a pressure that permits the reaction to occur while the produced phenol is distilled is preferable. In addition, preferably the breakdown reaction is implemented in an inert ambience such as under nitrogen streams.

Under these reaction conditions, preferably the 1,1,3-trisphenol is put through breakdown reaction for 1 to 10 hours or so. The breakdown reaction may be ended when, for example, there is no more distillation of phenol produced by breakdown reaction.

According to a preferable embodiment, the breakdown reaction of 1,1,3-trisphenol is implemented, for example, in an inert ambience for 3 to 6 hours or so at a temperature of 160 to 200° C. and pressure of 1 to 10 kPa after introducing a 1,1,3-trisphenol, alkali catalyst and solvent such as tetraethylene glycol or the like to the reaction container, while distilling out the phenol produced by breakdown reaction under agitation.

By causing a 1,1,3-trisphenol to undergo breakdown reaction as just explained, a bis(4-hydroxyphenyl)cyclohexene can be obtained at a reaction yield of approx. 90% if the conditions are favorable.

After the breakdown reaction in Step (B) has ended, it is possible, if an alkali catalyst was used in the breakdown reaction, to add aqueous solution of acid such as acetic acid or the like to the obtained reaction mixture to neutralize the alkali and use the obtained water/oil-containing mixture directly as the material for the next step, or Step (C), without crystallizing, filtering, or otherwise purifying the mixture. The reaction product can also be separated and purified if necessary, with the resulting product used as the material for Step (C).

For example, organic solvent that separates from water, such as methyl isobutyl ketone or the like, as well as water, are added to the aforementioned water/oil-containing mixture and the mixture is agitated, and the salt produced by the foregoing neutralization, and solvent (such as tetraethylene glycol) used in the breakdown reaction, are extracted into the water layer and separated and removed together with the water layer, after which the obtained oil layer is water-washed once or multiple times if necessary. Thereafter, the aforementioned organic solvent (such as methyl isobutyl ketone), phenol produced by breakdown, and other substances of low boiling point are distilled out of the obtained oil layer by means of distillation, etc. Thereafter, the distillation residue thus obtained may be used as the material for dehydrogenation reaction in the next step, or Step (C), or it may be mixed with a crystallization solvent to be crystallized and refined and the refined product may be used as the material for dehydrogenation reaction in the next step, or Step (C). Preferably the aforementioned crystallization solvent is, for example, aromatic hydrocarbon solvent such as toluene, xylene, or the like, aliphatic saturated hydrocarbon solvent such as n-hexane, n-heptane or the like, aliphatic ketone solvent such as methyl isobutyl ketone or the like, alicyclic saturated hydrocarbon solvent such as cyclohexane, cycloheptane or the like, or mixed solvent thereof, or the like.

In Step (B), the bis(4-hydroxyphenyl)cyclohexene expressed by General Formula (6) above, which is obtained by causing a 1,1,3-trisphenol expressed by General Formula (5) above to undergo breakdown reaction, is normally obtained in the form of an isomeric mixture of a 1,3-substitution product expressed by General Formula (10) above or 1,5-substitution product expressed by General Formula (11) above.

The mol ratio of the obtained isomeric mixture is not limited to any specific ratio depending on the material 1,1,3-trisphenol, reaction conditions, etc.; if there is no substitution group in the second position or sixth position of the cyclohexene-1-one, however, the isomeric mol ratio of the 1,3-substitution product or 1,5-substitution product is normally around 1 or a range of 0.6 to 1.5 or so, for example.

In addition, the obtained 1,3-substitution product expressed by General Formula (10) above and 1,5-substitution product expressed by General Formula (11) above have asymmetrical carbon atoms and thus each has an optical isomer such as an enantiomer or the like, and both, normally present as an optical isomer mixture, can be used as an effective material for Step (C).

In Step (D), a 2-cyclohexene-1-one or 3-hydroxycyclohexane-1-one and phenol are caused to react with each other in the presence of a catalyst to obtain a bis(4-hydroxyphenyl)cyclohexene expressed by General Formula (6) above through a single reaction, not apparently by way of trisphenol.

An example is shown below using Reaction Formula (3):

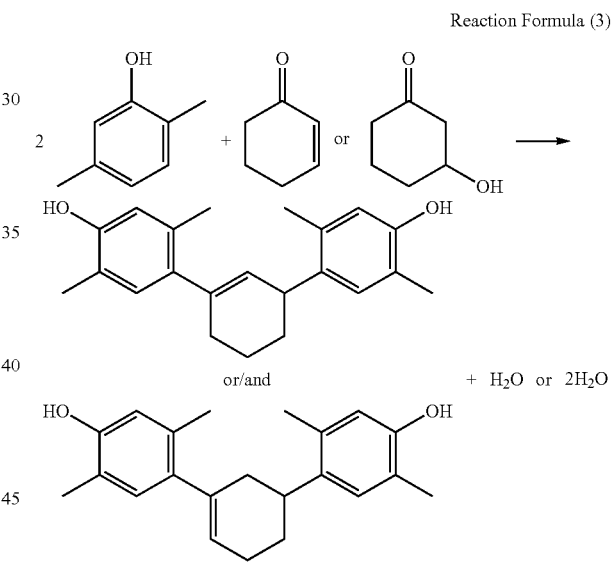

Reaction Formula (3)

From the viewpoint of yield, a phenol whose $R_5$ is not a hydrogen atom in General Formula (7) above is preferable, and accordingly the bis(4-hydroxyphenyl)cyclohexene to be obtained is preferably a bis(4-hydroxyphenyl)cyclohexene whose $R_5$ is not a hydrogen atom but an alkyl group, alkoxy group, aromatic hydrocarbon group, or halogen atom in General Formula (10) or General Formula (11), or more preferably a bis(4-hydroxyphenyl)cyclohexene whose $R_5$ is an alkyl group or alkoxy group, or most preferably a bis(4-hydroxyphenyl)cyclohexene whose $R_5$ is a methyl group or methoxy group.

For the reaction in Step (D), the mol ratios of materials, reaction temperature, catalyst, use quantity of catalyst, auxiliary catalyst, use quantity of auxiliary catalyst, reaction solvent, use quantity of reaction solvent, method of introducing the materials, etc., as well as specific examples, preferable ranges, and preferable quantities thereof, are the same as those explained in connection with Step (A).

In addition, any of the same known methods explained in connection with Step (A) can be used to treat the reaction liquid after the end of reaction or to isolate or refine the compound.

Under the manufacturing method proposed by the present invention, Step (C) that follows Step (B) or Step (D) mentioned above is where the 1,3- or 1,5-bis(4-hydroxyphenyl)cyclohexene obtained in Step (B) or Step (D) is dehydrogenated to obtain a 4,4"-dihydroxy-m-terphenyl expressed by General Formula (4) below as the target product of the manufacturing method proposed by the present invention.

General Formula (4)

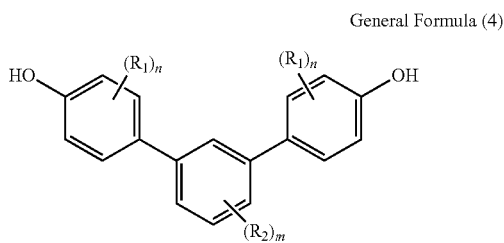

(In the formula, each $R_1$ and n is independently the same as the corresponding items in General Formula (3), respectively, while $R_2$ and m are the same as the corresponding items in General Formula (1) or General Formula (2), respectively.)

In addition, a preferable 4,4"-dihydroxy-m-terphenyl is expressed by General Formula (14) below:

General Formula (14)

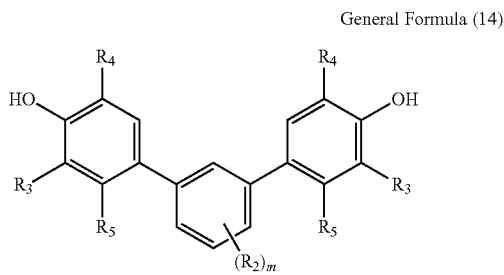

(In the formula, $R_2$ and m are the same as the corresponding items in General Formula (1) or General Formula (2), respectively, while each $R_3$, $R_4$, and $R_5$ are independently the same as the corresponding items in General Formula (7), respectively.)

In General Formula (14), preferably neither $R_3$ nor $R_4$ is a tertiary alkyl group, and when one is a tertiary alcohol, preferably the other is a hydrogen atom, primary alkyl group, or secondary alkyl group, and preferably the substitution position of $R_2$ is the fourth position or/and fifth position of the 1,3-phenylene group.

Additionally, if Step (A), Step (B), and Step (C) are implemented in this order, a 4,4"-dihydroxy-m-terphenyl whose $R_5$ is a hydrogen atom in General Formula (14) is preferable. If Step (D) and Step (C) are implemented in this order, on the other hand, a 4,4"-dihydroxy-m-terphenyl whose $R_5$ is not a hydrogen atom in General Formula (14) is preferable, where $R_5$ is more preferably an alkyl group or alkoxy group, or most preferably a methyl group or methoxy group.

Accordingly, the 4,4"-dihydroxy-m-terphenyl obtained from the manufacturing method proposed by the present invention corresponds to its materials, or specifically a 2-cyclohexene-1-one expressed by General Formula (1) above or 3-hydroxycyclohexane-1-one expressed by General Formula (2) above and phenol expressed by General Formula (3) above, where specific examples include 4,4"-dihydroxy-m-terphenyl, 3,3"-dimethyl-4,4"-dihydroxy-m-terphenyl, 3,3"-diethyl-4,4"dihydroxy-m-terphenyl, 3,3"-diisopropyl-4-4"-dihydroxy-m-terphenyl, 3,3"-dimethoxy-4,4"-dihydroxy-m-terphenyl, 3,3"-di-t-butyl-4,4"-dihydroxy-m-terphenyl, 3,3"-di-sec-butyl-4,4"-dihydroxy-m-terphenyl, 3,3"-dichloro-4,4"-dihydroxy-m-terphenyl, 3,3",5,5"-tetramethyl-4,4"-dihydroxy-m-terphenyl, 3,3"-di-t-butyl-5,5"-dimethyl-4,4"-dihydroxy-m-terphenyl, 3,3",5,5"-tetraisopropyl-4,4"-dihydroxy-m-terphenyl, 3,3"-diisopropyl-5,5"-dimethyl-4,4"-dihydroxy-m-terphenyl, 3,3",4,4"-tetrahydroxy-m-terphenyl, 3,3"-dicyclohexyl-4,4"-dihydroxy-m-terphenyl, 1,3-bis(4-hydroxyphenyl)-2-methyl benzene, 1,3-bis(4-hydroxyphenyl)-2-methoxy benzene, 1,3-bis(4-hydroxyphenyl)-2-phenyl benzene, 1,3-bis(4-hydroxyphenyl)-4-methyl benzene, 1,3-bis(4-hydroxyphenyl)-4-phenyl benzene, 1,3-bis(4-hydroxyphenyl)-4-cyclohexyl benzene, 1,3-bis(4-hydroxyphenyl)-5-methyl benzene, 1,3-bis(4-hydroxyphenyl)-5-t-butyl benzene, 1,3-bis(4-hydroxyphenyl)-5-phenyl benzene, 1,3-bis(4-hydroxyphenyl)-2-methyl-5-isopropyl benzene, 1,3-bis(4-hydroxyphenyl)-2,5,6-trimethyl benzene, 2,2",3,3",5,5"-hexamethyl-4,4"-dihydroxy-m-terphenyl, 3,3"-diphenyl-4,4"-dihydroxy-m-terphenyl, 2,2",5,5"-tetramethyl-4,4"-dihydroxy-m-terphenyl, 2,2"-dimethyl-5,5"-di-t-butyl-4,4"-dihydroxy-m-terphenyl, 2,2"-dimethyl-5,5"-dicyclohexyl-4,4"-dihydroxy-m-terphenyl, etc.

In Step (C), the bis(4-hydroxyphenyl)cyclohexene obtained in Step (B) or Step (D) is put through dehydrogenation reaction. The method to dehydrogenate the cyclohexene ring and thereby turn it into a benzene ring is not limited in any way, and any reaction method heretofore known can be used as deemed appropriate. However, a method to dehydrogenate the cyclohexene ring in the presence of a dehydrogenation catalyst is preferable.

An example is shown below using Reaction Formula (4):

Reaction Formula (4)

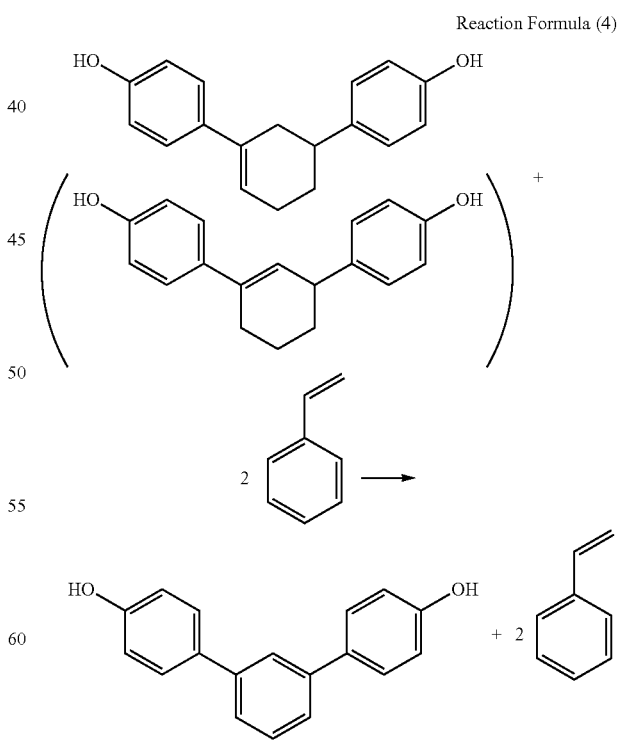

For the dehydrogenation catalyst, any dehydrogenation catalyst heretofore known can be used. For example, a nickel catalyst such as Raney nickel, reduced nickel, nickel-supported catalyst, or the like, cobalt catalyst such as Raney cobalt, reduced cobalt, cobalt-supported catalyst or the like, copper catalyst such as Raney copper or the like, palladium catalyst such as palladium oxide, palladium black, palladium/carbon or the like, platinum catalyst such as platinum black, platinum/carbon or the like, rhodium catalyst, chromium catalyst, or copper chromium catalyst, or the like is used. Among these, a platinum-group catalyst such as palladium or the like is preferable, of which palladium catalyst is favorably used.

Such dehydrogenation catalyst is used by a range of preferably 0.1 to 20 parts by weight, or more preferably 0.2 to 10 parts by weight, per 100 parts by weight of the bis(4-hydroxyphenyl)cyclohexane.

In this dehydrogenation reaction, a hydrogen receptor may or may not be coexistent. If disproportionation reaction is implemented without using any hydrogen receptor, a 1,3-bis(4-hydroxyphenyl)cyclohexane is obtained as a byproduct when a 4,4"-dihydroxy-m-terphenyl is produced. To obtain the target product at high purity, preferably the reaction is implemented using a dehydrogenation catalyst in the presence of a hydrogen receptor.

Such hydrogen receptor is not limited in any way, but styrene such as α-methyl styrene or the like, nitrobenzene, methyl isobutyl ketone, phenol, etc., is favorably used, for example. In addition, the dehydrogenation reaction temperature is preferably in a range of 100 to 250° C., or more preferably in a range of 130 to 200° C.

The dehydrogenation reaction can be implemented in gas phase, but preferably it is implemented in a solution state for ease of operation, in which case preferably a reaction solvent is used. Such reaction solvent may be aliphatic alcohol solvent such as ethylene glycol, 2-propanol, 2-butanol, or the like, aliphatic ketone solvent such as methyl isobutyl ketone, acetone, diisopropyl ketone or the like, aromatic hydrocarbon solvent such as toluene, xylene, ethyl benzene, or the like. In addition, preferably the reaction is implemented at normal pressure. Under these reaction conditions, preferably the dehydrogenation reaction ends in 3 to 10 hours or so.

The bis(4-hydroxyphenyl)cyclohexene thus obtained through Step (A) followed by Step (B), or through Step (D), is caused to undergo the dehydrogenation reaction in Step (C), and when the reaction is finished, the obtained reaction mixture is put through a normal method to separate the catalyst, and then crystallized, filtered, etc., to obtain a crude product of the target of the present invention, or specifically 4,4"-dihydroxy-m-terphenyl, which is then crystallized, filtered, or otherwise refined again, if necessary, to obtain the target product at high purity.

According to the present invention, preferably the target 4,4"-dihydroxy-m-terphenyl can be obtained this way at a yield of approx. 40% or greater, from the starting materials including a 2-cyclohexene-1-one expressed by General Formula (1) above or 3-hydroxycyclohexane-1-one expressed by General Formula (2) above and phenol expressed by General Formula (3) above.

Also regarding the thus-obtained compound proposed by the present application for patent, their purposes of use as well as derivatives obtained by substituting the phenolic hydroxyl group or according to any other known method are explained in detail.

For example, a 1,3-bis{4-[2-(3-oxetanyl)]butoxyphenyl}benzene, etc., can be obtained by reacting the compound proposed by the present application for patent with a 2-(3-oxetanyl)butyltosylate, and this 1,3-bis{4-[2-(3-oxetanyl)]butoxyphenyl}benzene, etc., can be used as the material to obtain an oxetane resin.

In addition, a 1,3-bis{4-[(6-diazo-5-oxonaphthyl)sulfonyloxy]phenyl}benzene, etc., can be obtained by reacting with a 1,2-naphtoquinonediazido-5-sulfonic acid chloride, and the 1,3-bis{4-[(6-diazo-5-oxonaphthyl)sulfonyloxy]phenyl}benzene, etc., can be used in a photosensitive composition.

In addition, a 1,3-bis(3-methyl(2H,4H-benzo[3,4-e]1,3-oxazine-6-yl))benzene, etc., can be obtained by reacting with a methyl amine and formaldehyde, and the 1,3-bis(3-methyl(2H,4H-benzo[3,4-e]1,3-oxazine-6-yl))benzene, etc., can be used as the material for a resin.

In addition, a 4,4"-di(glycidyloxy)-m-terphenyl, etc., can be obtained by reacting with an epichlorohydrin, and the 4,4"-di(glycidyloxy)-m-terphenyl, etc., can be used as the material to obtain an epoxy resin.

In addition, a 4,4"-dihydroxy-3,3",5,5"-tetrahydroxymethyl-m-terphenyl, etc., can be obtained by reacting with a formaldehyde. Furthermore, a 4,4"-dihydroxy-3,3",5,5"-tetramethoxymethyl-m-terphenyl, etc., can be obtained by causing these compounds to react with a methanol, for use as a cross-linking material, etc., in various applications.

In addition, a 4,4"-di(2-hydroxyethoxy)-m-terphenyl, etc., can be obtained by reacting with an ethylene carbonate, and the 4,4"-di(2-hydroxyethoxy)-m-terphenyl, etc., can be used as a resin material for polyester, polycarbonate, etc.

As for other applications for use, the compound proposed by the present application for patent, because it has multiple phenolic hydroxyl groups, is expected to be useful as a resin material for cyanate resin, polycarbonate, polyester, novolak, resol, etc., as a hardening agent for epoxy resin, as an additive for i-ray resist, or as an antioxidant.

EXAMPLES

The present invention is explained in detail below using examples; it should be noted, however, the present invention is not limited to the following examples:

Example 1

Synthesis of 4,4"-dihydroxy-m-terphenyl

Step (A): (Synthesis of 1,1,3-tris(4-hydroxyphenyl)cyclohexane)

1412 g of phenol, 78.2 g of 35% hydrochloric acid, 15.2 g of dodecyl mercaptan, and 144 g of methanol were introduced to a 4-way flask of 3 liters in capacity, into which 144 g of 2-cyclohexene-1-one was dripped over 10 hours in a nitrogen ambience with the liquid temperature kept at 30 to 32° C., at the end of which the mixture was agitated for 46 hours at 30° C. After the end of reaction, aqueous sodium hydroxide solution was added to neutralize the liquid, which was then heated to distill out the methanol. Thereafter, the water layer was separated and removed and the obtained oil layer was mixed with water and methyl isobutyl ketone, after which the mixture was agitated and water-washed to separate and remove the water layer. From the obtained oil layer, the methyl isobutyl ketone and unreacted phenol were distilled out under reduced pressure and removed. Toluene was added to the residue and the separated crystal was filtered out at room temperature and then dried to obtain a crude crystal of 1,1,3-tris(4-hydroxyphenyl)cyclohexane of 95% purity (according to the high-speed liquid chromatography).

This crude crystal was dissolved in methyl isobutyl ketone, and then water was added to water-wash the mixture, after which the water layer was separated. The obtained oil layer was condensed, after which toluene was added to the residue and the separated crystal was filtered out at room temperature and then dried to obtain 223.2 g of 1,1,3-tris(4-hydroxyphenyl)cyclohexane of 99.4% purity (according to the high-speed liquid chromatography).

Yield: 42% (yield with respect to 2-cyclohexene-1-one)

Molecular weight: 359 (M–H)⁻ (according to liquid chromatography mass spectrometry)

Melting point: 202° C. (according to differential scanning calorimetry)

$^1$H-NMR (400 MHz) measurement (solvent: DMSO-d6): Refer to Table 1.

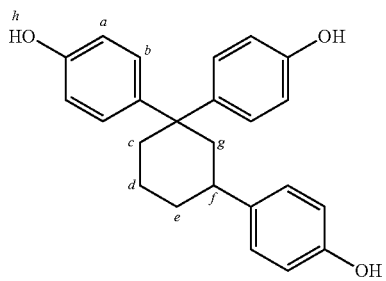 [SMILES: Oc1ccc(C2CCCC(c3ccc(O)cc3)(c3ccc(O)cc3)C2)cc1]

TABLE 1

| $^1$H-NMR (400 MHz) identification result (Internal starndard: Tetramethyl silane) | | | |
|---|---|---|---|
| Assignment | Shift value (ppm) | Signal | Number of protons |
| c~g | 1.38~2.67 | m | 9 |
| a, b | 6.61~7.21 | d × 6 | 12 |
| h | 9.4 | s | 3 |

Step (B): (Synthesis of 1,3-bis(4-hydroxyphenyl)-1-cyclohexene and 1,5-bis(4-hydroxyphenyl)-1-cyclohexene)

18.0 g of the 1,1,3-tris(4-hydroxyphenyl)cyclohexane obtained in Step (A), 9.0 g of tetraethylene glycol, and 1.3 g of 16% aqueous sodium hydroxide solution were introduced to a 4-way flask equipped with a thermometer, a cooler, and agitating wings, and the mixture was heated to 170° C. under agitation while reducing the pressure to 10 kPa, after which the temperature was maintained for another 9 hours while distilling out the produced phenol under agitation and at reduced pressure to cause breakdown reaction. After the end of reaction, the liquid was cooled to 100° C. and then neutralized by adding acetic acid. The liquid was further mixed with methyl isobutyl ketone and water and agitated, after which the water layer was separated. Water was added to the obtained oil layer and the mixture was agitated to separate the water layer, and this water-washing operation was performed three times. Thereafter, the solvent was distilled and removed from the water-washed oil layer, after which 18 g of toluene was added to separate, filter out, and dry the crystal to obtain 6 g of a mixture of 1,3-bis(4-hydroxyphenyl)-1-cyclohexene (A) and 1,5-bis(4-hydroxyphenyl)-1-cyclohexene (B) of 91% purity (according to the high-speed liquid chromatography) (ratio by high-speed liquid chromatography: A/B=49/51).

A part of this mixture was isolated by liquid chromatography and refined to obtain a mixture of 1,3-bis(4-hydroxyphenyl)-1-cyclohexene (A) and 1,5-bis(4-hydroxyphenyl)-1-cyclohexene (B) of 98% purity (according to high-speed liquid chromatography) (ratio by high-speed liquid chromatography: A/B=50/50), and the NMR, molecular weight, and melting point of this mixture were measured.

Molecular weight: 265 (M–H)⁻ (according to liquid chromatography mass spectrometry)

Melting point: 159° C. (according to differential scanning calorimetry)

$^1$H-NMR (400 MHz) measurement (solvent: CD$_3$OD): Refer to Table 2.

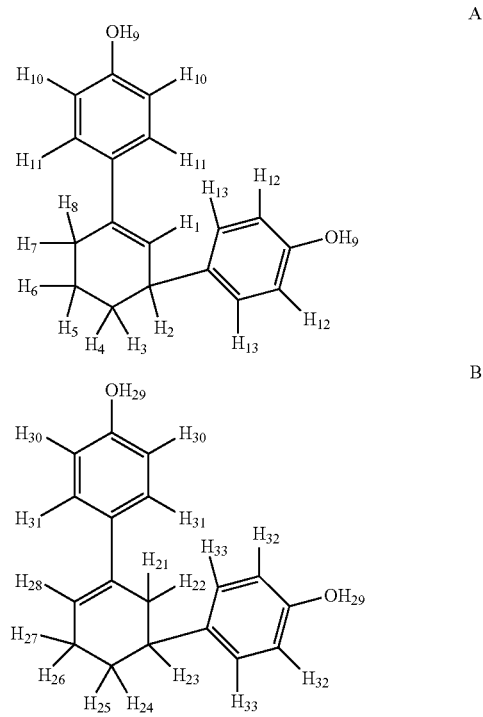

TABLE 2

| $^1$H-NMR (400 MHz) identification result (Internal starndard: Tetramethyl silane) | | | |
|---|---|---|---|
| Assignment | Shift value (ppm) | Signal | Number of protons |
| H3 | 1.42~1.51 | q | 0.4 |
| H5, H24 | 1.60~1.71 | m | 1.0 |
| H4, H6, H25 | 1.82~1.97 | m | 1.4 |
| H7, H8, H26, H21, H27 | 2.25~2.38 | m | 2.6 |
| H22 | 2.49~2.55 | d | 0.6 |
| H23 | 2.71~2.76 | m | 0.6 |
| H2 | 3.33~3.39 | m | 0.4 |
| H9, H29 | 5.11 | br | 2.0 |
| H1 | 5.92 | s | 0.4 |
| H28 | 5.98 | s | 0.6 |
| H10, H12, H30, H32 | 6.73~6.77 | m | 4.0 |
| H13, H33 | 7.00~7.06 | m | 2.0 |
| H11, H31 | 7.19~7.25 | m | 2.0 |

Step (C): (Synthesis of 4,4"-dihydroxy-m-terphenyl)

2.6 g of the 91% pure mixture of 1,3-bis(4-hydroxyphenyl)-1-cyclohexene and 1,5-bis(4-hydroxyphenyl)-1-cyclohexene obtained in Step (B), 15.6 g of methyl isobutyl ketone, 3.5 g of α-methyl styrene, and 0.2 g of 5% palladium carbon were introduced to an autoclave and agitated for 6 hours at 150° C. After the end of reaction, the reaction liquid was filtered to remove the 5% palladium carbon, and then the filtrate was condensed. The residue was dissolved in 3.2 g of ethyl acetate, after which 7.5 g of cyclohexane was added to the mixture and the separated crystal was filtered out and dried to obtain 1.9 g of 4,4"-dihydroxy-m-terphenyl of 99% purity (high-speed liquid chromatography).

Yield: 33% (with respect to trisphenol)
Molecular weight: 261 (M−H)⁻ (according to liquid chromatography mass spectrometry)
Melting point: 183° C. (according to differential scanning calorimetry)
$^1$H-NMR (400 MHz) measurement (solvent: DMSO-d6): Refer to Table 3.

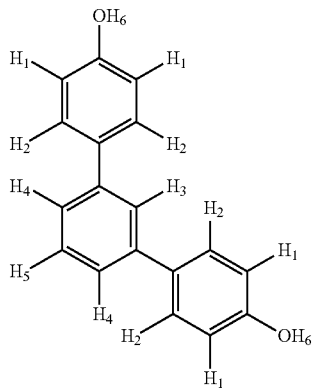

TABLE 3

| | $^1$H-NMR (400 MHz) identification result (Internal starndard: Tetramethyl silane) | | |
|---|---|---|---|
| Assignment | Shift value (ppm) | Signal | Number of protons |
| H1 | 6.92 | d | 4 |
| H4, H5 | 1.60~1.71 | m | 3 |
| H2 | 7.58 | d | 4 |
| H3 | 7.76 | s | 1 |
| H6 | 9.61 | s | 2 |

Example 2

Synthesis of 4,4"-dihydroxy-m-terphenyl 90 g of the 1,1,3-tris(4-hydroxyphenyl)cyclohexane obtained in Step (A) of Example 1, 45 g of tetraethylene glycol, 45 g of methanol, and 6.3 g of 16% aqueous sodium hydroxide solution were introduced to a 4-way flask, and the mixture was heated to 170° C. under agitation while reducing the pressure 10 kPa, after which the temperature was maintained for another 9 hours while distilling out the produced phenol under agitation to cause reaction. After the end of reaction, the liquid was cooled and then neutralized by adding acetic acid, and then mixed with water and methyl isobutyl ketone and agitated, followed by water washing [Step (B)].

After the water layer was separated, the oil layer was condensed or otherwise adjusted so that the concentration of the mixture of 1,3-bis(4-hydroxyphenyl)-1-cyclohexene and 1,5-bis(4-hydroxyphenyl)-1-cyclohexene became 17%. 79.6 g of the concentration-adjusted solution, 14.8 g of α-methyl styrene and 0.8 g of 5% palladium carbon were introduced to an autoclave and agitated for 6 hours at 150° C. After the reaction, the reaction liquid was filtered to remove the 5% palladium carbon, and then the methyl isobutyl ketone was distilled out, after which 40 g of toluene was added and the separated crystal was filtered out and dried to obtain 6.9 g of 4,4"-dihydroxy-m-terphenyl of 97% purity (high-speed liquid chromatography) [Step (C)].

Yield: 53% (with respect to trisphenol)

Example 3

[Synthesis of 3,3"-dimethyl-4,4"-dihydroxy-m-terphenyl]

Step (A): (Synthesis of 1,1,3-tris(3-methyl-4-hydroxyphenyl)cyclohexane)

1513.4 g of ortho-cresol, 73 g of 35% hydrochloric acid, 14.2 g of dodecyl mercaptan, and 134.4 g of methanol were introduced to a 4-way flask of 3 liters in capacity, into which 134.5 g of 2-cyclohexene-1-one was dripped over 3.5 hours in a nitrogen ambience with the liquid temperature kept at 30 to 32° C., at the end of which the liquid was agitated for 22 hours at 30 to 32° C. After the end of reaction, aqueous sodium hydroxide solution was added to neutralize the liquid, which was then heated to distill out the methanol. Thereafter, the water layer was separated and removed and the obtained oil layer was mixed with methyl isobutyl ketone and water, after which the mixture was agitated and water-washed to separate and remove the water layer. From the obtained oil layer, the methyl isobutyl ketone and unreacted ortho-cresol were distilled out under reduced pressure and removed. The residue was dissolved in 1-octanol, after which cyclohexane was added to separate the crystal, and the separated adduct crystal was filtered out at room temperature and then dried to obtain 522.5 g of adduct crystal of 1,1,3-tris(4-hydroxy-3-methyl phenyl)cyclohexane. This crystal contained 16% of solvent based on gas chromatography, and had a purity of 99.2% (excluding the solvent) based on high-speed liquid chromatography.

Yield: 77.9% (yield with respect to 2-cyclohexene-1-one)
Molecular weight: 401 (M−H)⁻ (according to liquid chromatography mass spectrometry)
$^1$H-NMR (400 MHz) measurement (solvent: CDCl₃): Refer to Table 4.

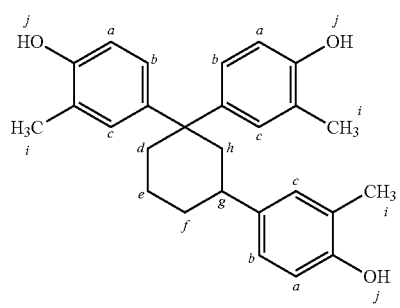 [SMILES: Cc1cc(C2CCCC(c3ccc(O)c(C)c3)(c3ccc(O)c(C)c3)C2)ccc1O]

TABLE 4

<sup>1</sup>H-NMR (400 MHz) identification result (Internal starndard: Tetramethyl silane)

| Assignment | Shift value (ppm) | Signal | Number of protons |
|---|---|---|---|
| d~h | 1.43~2.72 | m | 9 |
| i | 2.15, 2.23, 2.24 | s | 9 |
| j | 4.74 | s | 3 |
| a~c | 6.57~7.12 | m | 9 |

Step (B): (Synthesis of 1,3-bis(3-methyl-4-hydroxyphenyl)-1-cyclohexene and 1,5-bis(3-methyl-4-hydroxyphenyl)-1-cyclohexene)

236.8 g of the adduct crystal of 1,1,3-tris(3-methyl-4-hydroxyphenyl)cyclohexane obtained in Step (A) of Example 3, 50.3 g of tetraethylene glycol and 12.5 g of 16% aqueous sodium hydroxide solution were introduced to a 4-way flask equipped with a thermometer, a cooler, and agitating wings, and the mixture was heated to 190° C. and then breakdown reaction was implemented for 2 hours while distilling out the produced ortho-cresol at reduced pressure. After the end of reaction, the liquid was cooled and then neutralized by adding acetic acid, and further mixed with methyl isobutyl ketone and water and agitated, and then water-washed, to separate and remove the water layer. The methyl isobutyl ketone was distilled out of the obtained oil layer to obtain, as distillation residue, 132.3 g of a mixture of 1,3-bis(3-methyl-4-hydroxyphenyl)-1-cyclohexene (C) and 1,5-bis(3-methyl-4-hydroxyphenyl)-1-cyclohexene (D) of 86.8% purity (according to high-speed liquid chromatography) (ratio by high-speed liquid chromatography: C/D=56/44).

A part of this mixture was isolated by liquid chromatography and refined to obtain a mixture of 1,3-bis(3-methyl-4-hydroxyphenyl)-1-cyclohexene (C) and 1,5-bis(3-methyl-4-hydroxyphenyl)-1-cyclohexene (D) of 96.8% purity (according to high-speed liquid chromatography) (ratio by high-speed liquid chromatography: C/D=59/41), and the NMR of this mixture was measured.

Molecular weight: 293 (M–H)<sup>−</sup> (according to liquid chromatography mass spectrometry)

<sup>1</sup>H-NMR (400 MHz) measurement (solvent: CDCl₃): Refer to Table 5.

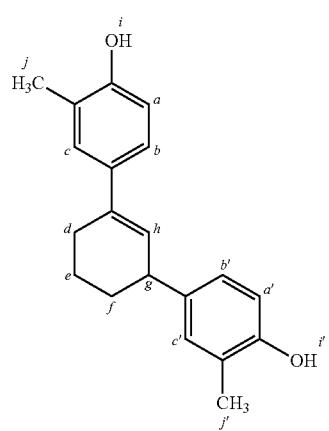

C

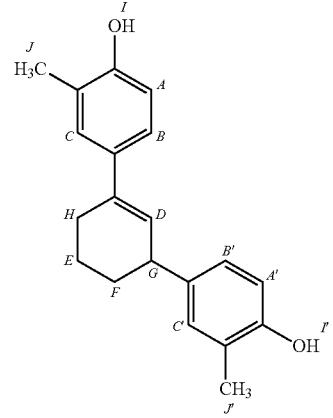

D

TABLE 5

<sup>1</sup>H-NMR (400 MHz) identification result (Internal starndard: Tetramethyl silane)

| Assignment | Shift value (ppm) | Signal | Number of protons |
|---|---|---|---|
| a~c, a'~c' A~C, A'~C' | 6.69~7.22 | m | 6 |
| d~f, D~F | 1.52~2.59 | m | 6 |
| g, G | 3.43~3.50, 2.79~2.87 | m | 1 |
| h, H | 6.01, 6.06 | s | 1 |
| i, i', I, I' | 4.61, 4.63, 4.67, 4.70 | s | 2 |
| j, j', J, J' | 2.23~2.26 | m | 6 |

Step (C): (Synthesis of 3,3''-dimethyl-4,4''-dihydroxy-m-terphenyl)

35.3 g of the mixture obtained in Step (B) of Example 3, 17.7 g of ethylene glycol, 35.5 g of α-methyl styrene, and 2.2 g of 5% palladium carbon were introduced to a 4-way flask of 200 ml in capacity, and reacted for 4 hours at a liquid temperature of 145 to 146° C. After the palladium carbon was removed from the resultant liquid of reaction, the methyl isobutyl ketone and water were added to water-wash the liquid, thereby separating and removing the water layer. The methyl isobutyl ketone was then distilled out of the obtained oil layer, to obtain 30.4 g of distillation residue of 85.1% purity (according to high-speed liquid chromatography). 5 g of this residue was dissolved by adding 2.5 g of 1-octanol, after which 10 g of cyclohexane was added to separate and filter out the crystal, to obtain 2.7 g of adduct crystal (cyclohexane adduct) of 3,3''-dimethyl-4,4''-dihydroxy-m-terphenyl of 96.3% purity (according to high-speed liquid chromatography).

A part of this crystal was isolated by liquid chromatography and refined to obtain a 3,3''-dimethyl-4,4''-dihydroxy-m-terphenyl of 99.9% purity (according to high-speed liquid chromatography), and its NMR and melting point were measured.

Molecular weight: 289 (M–H)<sup>−</sup> (according to liquid chromatography mass spectrometry)

Melting point: 138.2° C. (according to differential scanning calorimetry)

<sup>1</sup>H-NMR (400 MHz) measurement (solvent: CDCl₃): Refer to Table 6.

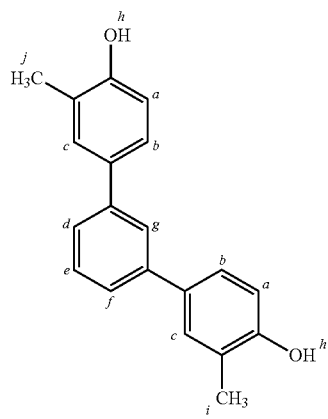 [SMILES: Cc1cc(-c2cccc(-c3ccc(O)c(C)c3)c2)ccc1O]

TABLE 6

$^1$H-NMR (400 MHz) identification result (Internal starndard: Tetramethyl silane)

| Assignment | Shift value (ppm) | Signal | Number of protons |
| --- | --- | --- | --- |
| a | 6.84, 6.86 | d | 2 |
| b~f | 7.35~7.48 | m | 7 |
| g | 7.68 | s | 1 |
| h | 4.76 | s | 2 |
| i | 2.33 | s | 6 |

Example 4

Synthesis of 3,3"-diphenyl-4,4"-dihydroxy-m-terphenyl

Step (A): Synthesis of 1,1,3-tris(3-phenyl-4-hydroxyphenyl)cyclohexane 177.0 g of 2-phenyl phenol, 1.0 g of dodecyl mercaptan, and 17.7 g of methanol were introduced to a 4-way flask of 500 ml in capacity, and after the mixture was heated to a liquid temperature of 41° C. in a nitrogen ambience, hydrogen chloride gas was blown into the system until the system was saturated by hydrogen chloride gas. 20.0 g of 2-cyclohexene-1-one was dripped into the saturated liquid over 4 hours under agitation with the internal temperature kept at 41° C., at the end of which the mixture was agitated for 19 hours at 41° C. while blowing in hydrogen chloride gas. After the end of reaction, 16% aqueous sodium hydroxide solution was added to neutralize the liquid, which was then heated to separate and remove the water layer. Thereafter, toluene and water were added to the liquid, which was then agitated and water-washed to separate the water layer, and toluene and unreacted 2-phenyl phenol were distilled out of the obtained oil layer at reduced pressure, to obtain 95.2 g of 1,1,3-tris(3-phenyl-4-hydroxyphenyl)cyclohexane of 48.0% purity (according to high-speed liquid chromatography).

A part of this was isolated by liquid chromatography and refined, and the obtained product of high purity was put through proton NMR analysis and molecular weight measurement, to confirm that it was the target product.

Molecular weight: 587 (M−H)⁻ (according to liquid chromatography mass spectrometry)

$^1$H-NMR (400 MHz) measurement (solvent: DMSO-d6): Refer to Table 7.

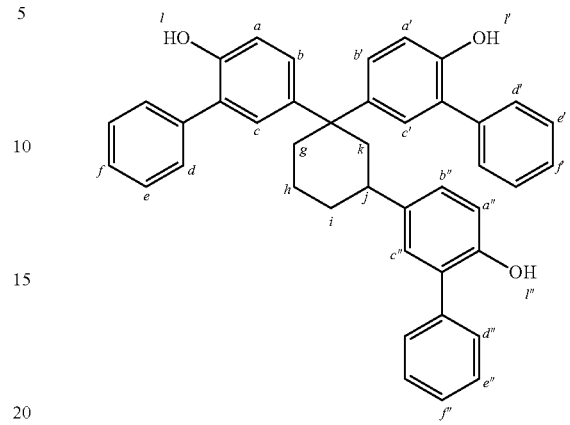

TABLE 7

$^1$H-NMR (400 MHz) identification result (Internal starndard: Tetramethyl silane)

| Assignment | Shift value (ppm) | Signal | Number of protons |
| --- | --- | --- | --- |
| g~k | 1.53~2.83 | m | 9 |
| a, a', a" | 6.77~6.96 | d × 3 | 3 |
| b~f, b'~f', b"~f" | 7.03~7.56 | m | 21 |
| l, l', l" | 9.25~9.40 | s × 3 | 3 |

Step (B): Synthesis of 1,3-bis(3-phenyl-4-hydroxyphenyl)-1-cyclohexene and 1,5-bis(3-phenyl-4-hydroxyphenyl)-1-cyclohexene 61.3 g of the 1,1,3-tris(3-phenyl-4-hydroxyphenyl)cyclohexane obtained in Step (A) of Example 4, 7.4 g of tetraethylene glycol, and 1.3 g of 16% aqueous sodium hydroxide solution were introduced to a 4-way flask of 200 ml in capacity equipped with a thermometer, a cooler, and agitating wings, and after the mixture was heated to a liquid temperature of 200° C., breakdown reaction was implemented for 3 hours while distilling the 2-phenyl phenol out of the reaction system at reduced pressure. After the end of reaction, the liquid was cooled and then neutralized by adding acetic acid, after which the liquid was further mixed with methyl isobutyl ketone and water and agitated and dissolved to separate and remove the water layer. The methyl isobutyl ketone was distilled out of the obtained oil layer, to obtain, as distillation residue, 37.8 g of a mixture of 1,3-bis(3-phenyl-4-hydroxyphenyl)-1-cyclohexene (Compound E) and 1,5-bis(3-phenyl-4-hydroxyphenyl)-1-cyclohexene (Compound F) (59.4% in purity according to high-speed liquid chromatography).

A part of this mixture was isolated by liquid chromatography and refined, and the obtained product of pure purity was put through proton NMR analysis and molecular weight measurement, to confirm that it was the target product.

Molecular weight: 417 (M−H)⁻ (according to liquid chromatography mass spectrometry)

$^1$H-NMR (400 MHz) measurement (solvent: CDCl$_3$): Refer to Table 8.

Compound E

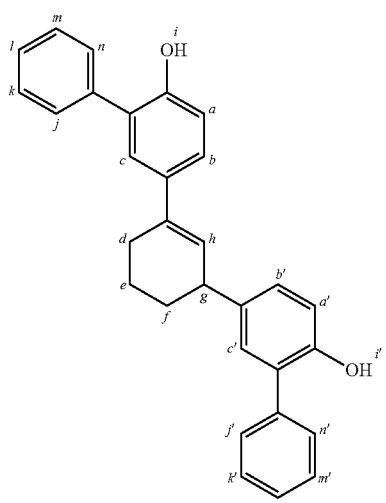

Compound F

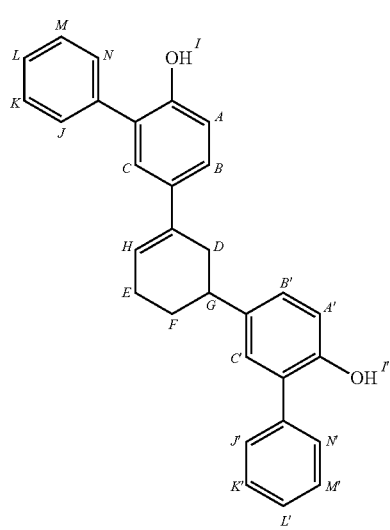

autoclave and reacted for 4.5 hours at 140 to 150° C. After the palladium carbon was removed from the resultant liquid of reaction, the methyl isobutyl ketone was distilled out of the obtained oil layer, to obtain 9.2 g of the target product as residue (77.4% in purity, according to high-speed liquid chromatography).

Using this residue, 3,3"-diphenyl-4,4"-dihydroxy-m-terphenyl (99.1% in purity according to high-speed liquid chromatography) was isolated and refined by liquid chromatography.

Molecular weight: 413 (M−H)⁻ (according to liquid chromatography mass spectrometry)

Melting point: Could not be confirmed (according to differential scanning calorimetry)

$^1$H-NMR (400 MHz) measurement (solvent: DMSO-d6): Refer to Table 9.

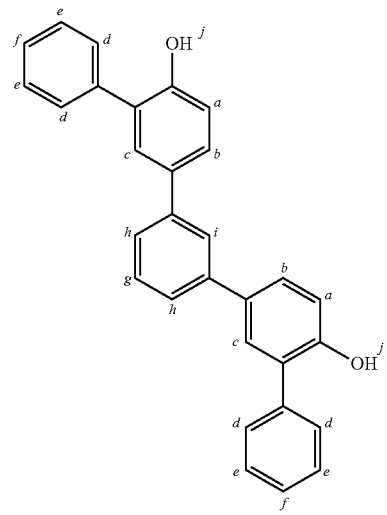 [SMILES: Oc1ccc(-c2cccc(-c3ccc(O)c(-c4ccccc4)c3)c2)cc1-c1ccccc1]

TABLE 9

$^1$H-NMR (400 MHz) identification result (Internal starndard: Tetramethyl silane)

| Assignment | Shift value (ppm) | Signal | Number of protons |
|---|---|---|---|
| a | 7.06, 7.08 | d | 2 |
| b~h | 7.30~7.66 | m | 17 |
| i | 7.84 | s | 1 |
| j | 9.72 | s | 2 |

Example 5

Synthesis of 2,2",5,5"-tetramethyl-4,4"-dihydroxy-m-terphenyl

Step (D): Synthesis of 1,3-bis(2,5-dimethyl-4-hydroxyphenyl)-1-cyclohexene and 1,5-bis(2,5-dimethyl-4-hydroxyphenyl)-1-cyclohexene 229.4 g of 2,5-xylenol, 1.03 g of dodecyl mercaptan, and 102.0 g of methanol were introduced to a 4-way flask of 1 liter in capacity equipped with a thermometer and agitator, and after the mixture was heated to a liquid temperature of 39° C. in a nitrogen ambience, hydrogen chloride gas was blown into

TABLE 8

$^1$H-NMR (400 MHz) identification result (Internal starndard: Tetramethyl silane)

| Assignment | Shift value (ppm) | Signal | Number of protons |
|---|---|---|---|
| a~c, a'~c' A~C, A'~C' j~n, j'~n' J~N, J'~N' | 6.89~7.48 | m | 16 |
| d~f, D~F | 1.58~2.72 | m | 6 |
| g, G | 2.86~2.94, 3.51~3.56 | m | 1 |
| h, H | 6.10~6.12 | m | 1 |
| i, i', I, I' | 5.15, 5.16, 5.20, 5.22 | s | 2 |

Step (C): Synthesis of 3,3"-diphenyl-4,4"-dihydroxy-m-terphenyl 12.6 g of the mixture obtained in Step (B) of Example 4, 37.8 g of methyl isobutyl ketone, 7.8 g of α-methyl styrene, and 5.22 g of 5% palladium carbon were introduced to an the system until the system was saturated by hydrogen chloride gas. A mixed liquid of 20.0 g of 2-cyclohexene-1-one, 25.6 g of 2,5-xylenol, and 25.6 g of methanol was dripped into the saturated liquid over 2 hours under agitation with the internal temperature kept at 39 to 41° C., at the end of which the mixture was agitated for 27 hours at 39 to 41° C. while blowing in hydrogen chloride gas. During the course of reaction, a part of the reaction liquid was collected and analyzed by high-speed liquid chromatography mass spectrometry, and as a result two peaks of the same molecular weight as with the target product were detected at approximately similar holding times. After the end of reaction, aqueous sodium hydroxide solution was added to neutralize the liquid. Methyl isobutyl ketone was added, and the mixture was then heated to 60° C. to dissolve the separated crystal, after which the water layer was separated and removed. The obtained oil layer was mixed with water and agitated and then kept stationary to separate and remove the water layer, and this water-washing operation was performed twice. The water-washed oil layer was condensed at reduced pressure to remove the solvent and separate the crystal, which was then cooled and then filtered to obtain crude crystal. The primary constituent of the crystal corresponded, of the aforementioned two detected peak constituents of the same molecular weight as with the target product, to the peak constituent associated with the slightly longer holding time. Methyl isobutyl ketone was added to dissolve the obtained crude crystal, after which the liquid was cooled and the separated crystal was filtered out and dried to obtain 17.7 g of white crystal of 98.7% purity (according to high-speed liquid chromatography). Based on the result of NMR analysis, this white crystal was 1,5-bis(2,5-dimethyl-4-hydroxyphenyl)-1-cyclohexene.

Molecular weight: 323 (M+H)$^+$ (according to liquid chromatography mass spectrometry)

Melting point: 247° C. (according to differential scanning calorimetry)

$^1$H-NMR (400 MHz) measurement (solvent: DMSO-d6): Refer to Table 10.

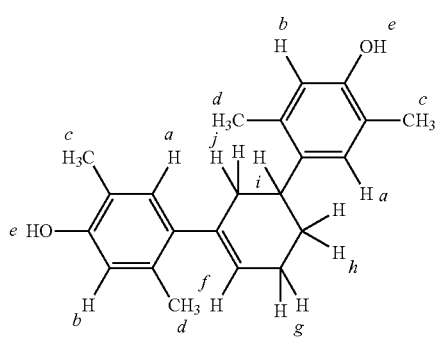 [SMILES: Cc1cc(C2=CCCC(c3cc(C)c(O)cc3C)C2)c(C)cc1O]

TABLE 10

$^1$H-NMR (400 MHz) identification result (Internal starndard: Tetramethyl silane)

| Assignment | Shift value (ppm) | Signal | Number of protons |
|---|---|---|---|
| a, b | 6.54, 6.55, 6.76, 6.90 | s × 4 | 4 |
| c, d | 2.04, 2.06, 2.14, 2.18 | s × 4 | 12 |
| e | 8.86, 8.99 | s × 2 | 2 |
| f | 5.48 | s | 1 |
| g | 2.22~2.34 | m | 2 |

TABLE 10-continued $^1$H-NMR (400 MHz) identification result (Internal starndard: Tetramethyl silane)

| Assignment | Shift value (ppm) | Signal | Number of protons |
|---|---|---|---|
| h | 1.64~1.78 | m | 2 |
| i | 2.87~2.98 | m | 1 |
| j | 2.12~2.23 | m | 2 |

In addition, the two peak constituents having the same molecular weight as the target product were isolated by chromatography from a part of the reaction liquid collected during the course of reaction above, to obtain a mixture of the two constituents. Based on the result of NMR analysis, this turned out to be a mixture of 1,3-bis(2,5-dimethyl-4-hydroxyphenyl)-1-cyclohexene and 1,5-bis(2,5-dimethyl-4-hydroxyphenyl)-1-cyclohexene.

Molecular weight: 323 (M+H)$^+$ $^1$H-NMR (400 MHz) measurement (solvent: DMSO-d6): Refer to Table 11.

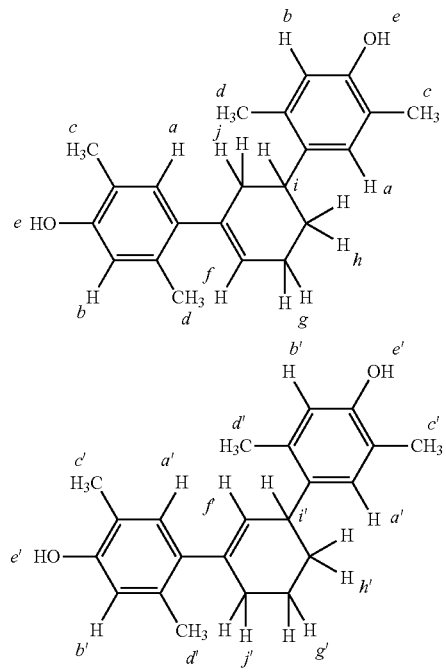

TABLE 11

$^1$H-NMR (400 MHz) identification result (Internal starndard: Tetramethyl silane)

| Assignment | Shift value (ppm) | Signal | Number of protons |
|---|---|---|---|
| a, a', b, b' | 6.54~6.90 | | 4 |
| c, c', d, d', g, g', j, j' | 1.89~2.34 | | 16 |
| e, e' | 8.85, 8.87, 8.99, 9.00 | s × 4 | 2 |
| f, f' | 5.30, 5.48 | s × 2 | 1 |
| h, h' | 1.38~1.43, 1.64~1.78 | m × 2 | 2 |
| i, i' | 2.87~2.98, 3.54~3.60 | m × 2 | 1 |

Step (C): Synthesis of 2,2″,5,5″-tetramethyl-4,4″-dihydroxy-m-terphenyl 3.0 g of the 98.7% pure 1,5-bis(2,5-dimethyl-4-hydroxyphenyl)-1-cyclohexene obtained in Step (D) of Example 5, 30 g of methyl isobutyl ketone, 3.0 g of α-methyl styrene, and 0.63 g of 5% palladium carbon were introduced to an autoclave and then heated to 150° C. to be reacted for 46.5 hours at the same temperature under agitation. After heating, 0.63 g of 5% palladium carbon was added after 18 hours and again after 34 hours, respectively. The mixture was heated further to 190° C. and agitated for 6 hours at the same temperature to cause reaction, after which the palladium carbon was filtered out and the obtained filtrate was condensed. The obtained residue was dissolved in methyl isobutyl ketone to separate the crystal, which was then filtered out and dried to obtain 1.4 g of 2,2″,5,5″-tetramethyl-4,4″-dihydroxy-m-terphenyl of 94.5% purity (according to high-speed liquid chromatography).

Yield: 46.3% (yield with respect to 1,5-bis(2,5-dimethyl-4-hydroxyphenyl)-1-cyclohexene)

Molecular weight: 317 (M–H)⁻ (according to liquid chromatography mass spectrometry)

Melting point: 238.3° C. (according to differential scanning calorimetry) $^1$H-NMR (400 MHz) measurement (solvent: DMSO-d6): Refer to Table 12.

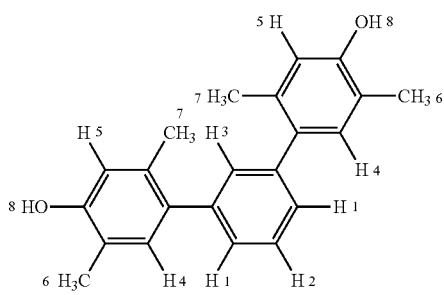 [SMILES: Cc1cc(-c2cccc(-c3cc(C)c(O)cc3C)c2)c(C)cc1O]

TABLE 12

| $^1$H-NMR (400 MHz) identification result (Internal starndard: Tetramethyl silane) | | | |
|---|---|---|---|
| Assignment | Shift value (ppm) | Signal | Number of protons |
| H6, H7 | 2.13, 2.18 | s | 12 |
| H5 | 6.72 | s | 2 |
| H4 | 6.95 | s | 2 |
| H3 | 7.14 | s | 1 |
| H1 | 7.19 | d | 2 |
| H2 | 7.4 | t | 1 |
| H8 | 9.23 | s | 2 |

Example 6

19.6 g of phenol and 4.0 g of P-toluene sulfonic acid monohydrate were introduced to a 100-ml test tube and the mixture was heated to a liquid temperature of 50° C., after which 2.1 g of 2-cyclohexene-1-one was added intermittently over 2 hours, at the end of which the mixture was reacted for 68 hours at 50° C. When the reaction liquid was analyzed, production of 1,1,3-tris(4-hydroxyphenyl)cyclohexane was confirmed.

Thereafter, the mixture was agitated further for 6 hours at 100° C. and 5 hours at 150° C.

When the resultant liquid of reaction was analyzed by high-speed liquid chromatography (calibration curve method), it contained 4,4″-dihydroxy-m-terphenyl at a yield of 20% and 1,3-bis(4-hydroxyphenyl)cyclohexane at a yield of 46%.

Reference example As explained below, a 3-hydroxycyclohexane-1-one can also be adopted as a material in Step (A) of the aforementioned examples.

Synthesis of 1,1,3-tris(4-hydroxyphenyl)cyclohexane 41.6 g of phenol, 3.2 g of 35% hydrochloric acid, and 0.5 g of dodecyl mercaptan were introduced to a 4-way flask of 200 ml in capacity and the mixture was heated to 40° C. in a nitrogen ambience, after which 10.7 g of 3-hydroxycyclohexane-1-one was dripped over 3 hours, at the end of which the mixture was agitated for 79 hours at 40° C. to cause reaction. When the resultant liquid of reaction was analyzed by high-speed liquid chromatography, the composition value (area percentage/excluding phenol) of 1,1,3-tris(4-hydroxyphenyl)cyclohexane was 61%. The yield calculated from this composition value was 59% (with respect to 3-hydroxycyclohexane-1-one).

After the end of reaction, the primary product was isolated from the reaction liquid by means of liquid chromatography, and based on the results of NMR and liquid chromatography mass spectrometry, it was confirmed to be the target product 1,1,3-tris(4-hydroxyphenyl)cyclohexane.

The invention claimed is:

1. A method of manufacturing 4,4″-dihydroxy-m-terphenyl expressed by General Formula (4) below, characterized by using a 2-cyclohexene-1-one expressed by General Formula (1) below or 3-hydroxycyclohexane-1-one expressed by General Formula (2) below, and phenol expressed by General Formula (3) below as materials and implementing Step (A), Step (B) and Step (C) below, in this order, or Step (D) and Step (C) below, in this order:

General Formula (1)

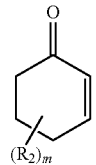

General Formula (2)

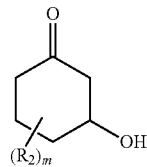

(in the formulas, each $R_2$ independently represents an alkyl group, alkoxy group, aromatic hydrocarbon group, or halogen atom, while m indicates 0 or an integer of 1 to 4, where $R_2$ substitution does not occur in a third position when m is 1 or greater, and when m is 2 or greater, $R_2$'s may be identical or different, and $R_2$ substitution does not occur in two positions of a same carbon atom; in addition, $R_2$ and m in General Formula (1) may be iden tical to or different from R₂ and m in General Formula (2), respectively);

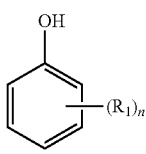

General Formula (3)

(in the formula, each R₁ independently represents an alkyl group, alkoxy group, aromatic hydrocarbon group, halogen atom, or hydroxyl group, while n indicates 0 or an integer of 1 to 4, where R₁'s may be identical or different when n is 2 or greater);

Step (A): Step to obtain a 1,1,3-trisphenol expressed by General Formula (5) below by causing the 2-cyclohexene-1-one or 3-hydroxycyclohexane-1-one and phenol to react with each other in a presence of a catalyst;

Step (B): Step to obtain a bis(4-hydroxyphenyl)cyclohexene expressed by General Formula (6) below by causing the 1,1,3-trisphenol to undergo breakdown reaction;

Step (C): Step to obtain a 4,4"-dihydroxy-m-terphenyl by dehydrogenating the bis(4-hydroxyphenyl)cyclohexene;

Step (D): Step to obtain a bis(4-hydroxyphenyl)cyclohexene expressed by General Formula (6) below by causing the 2-cyclohexene-1-one or 3-hydroxycyclohexane-1-one and phenol to react with each other in a presence of a catalyst;

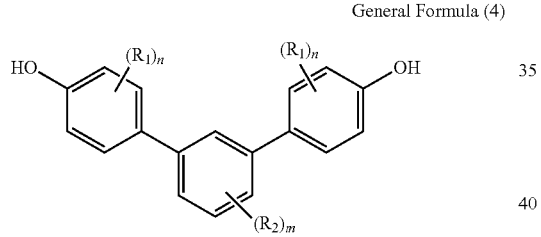

General Formula (4)

(in the formula, each R₁ and n is independently the same as corresponding items in General Formula (3), while R₂ and m are the same as corresponding items in General Formula (1) or General Formula (2);

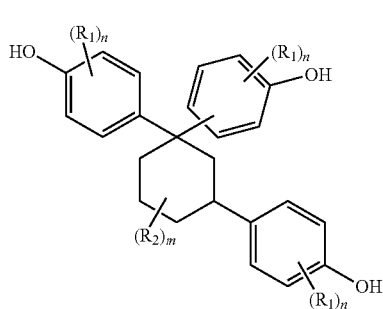

General Formula (5)

(in the formula, each R₁ and n is independently the same as corresponding items in General Formula (3), while R₂ and m are the same as corresponding items in General Formula (1) or General Formula (2);

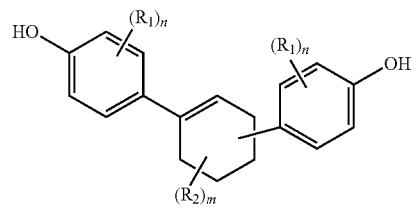

General Formula (6)

(in the formula, each R₁ and n is independently the same as corresponding items in General Formula (3), while R₂ and m are the same as corresponding items in General Formula (1) or General Formula (2), and a binding position of a 4-hydroxyphenyl group having no fixed binding position is a third position or fifth position of a cyclohexene ring).

* * * * *